United States Patent
Poon et al.

(10) Patent No.: US 9,687,664 B2
(45) Date of Patent: Jun. 27, 2017

(54) MULTI-ELEMENT COUPLER FOR GENERATION OF ELECTROMAGNETIC ENERGY

(71) Applicant: The Board of Trustees of the Leland Stanford Junior University, Palo Alto, CA (US)

(72) Inventors: Ada Shuk Yan Poon, Redwood City, CA (US); Alexander Jueshyan Yeh, Los Altos Hills, CA (US); Yuji Tanabe, Cupertino, CA (US); John Ho, Palo Alto, CA (US); Sanghoek Kim, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 15/022,374

(22) PCT Filed: Sep. 16, 2014

(86) PCT No.: PCT/US2014/055885
§ 371 (c)(1),
(2) Date: Mar. 16, 2016

(87) PCT Pub. No.: WO2015/039108
PCT Pub. Date: Mar. 19, 2015

(65) Prior Publication Data
US 2016/0220828 A1 Aug. 4, 2016

Related U.S. Application Data

(60) Provisional application No. 61/913,164, filed on Dec. 6, 2013, provisional application No. 61/878,436, filed on Sep. 16, 2013.

(51) Int. Cl.
*A61N 1/378* (2006.01)
*A61N 1/36* (2006.01)
(Continued)

(52) U.S. Cl.
CPC .......... *A61N 1/3787* (2013.01); *A61B 5/0008* (2013.01); *A61B 5/0013* (2013.01);
(Continued)

(58) Field of Classification Search
None
See application file for complete search history.

(56) References Cited

U.S. PATENT DOCUMENTS

| 5,324,316 A | 6/1994 | Schulman et al. |
| 5,735,887 A | 4/1998 | Barreras, Sr. et al. |

(Continued)

FOREIGN PATENT DOCUMENTS

| CN | 105744986 A | 7/2016 |
| EP | 1171190 A1 | 1/2002 |

(Continued)

OTHER PUBLICATIONS

"U.S. Appl. No. 15/200,543, Preliminary Amendment filed Aug. 4, 2016", 5 pgs.
(Continued)

*Primary Examiner* — Brian T Gedeon
(74) *Attorney, Agent, or Firm* — Schwegman Lundberg & Woessner, P.A.

(57) ABSTRACT

Implantable devices and/or sensors can be wirelessly powered by controlling and propagating electromagnetic waves in a patient's tissue. Such implantable devices/sensors can be implanted at target locations in a patient, to stimulate areas such as the heart, brain, spinal cord, or muscle tissue, and/or to sense biological, physiological, chemical attributes of the blood, tissue, and other patient parameters. The
(Continued)

propagating electromagnetic waves can be generated with sub-wavelength structures configured to manipulate evanescent fields outside of tissue to generate the propagating waves inside the tissue. Methods of use are also described.

26 Claims, 27 Drawing Sheets

(51) Int. Cl.
| | |
|---|---|
| A61N 1/372 | (2006.01) |
| A61N 1/05 | (2006.01) |
| A61M 5/142 | (2006.01) |
| A61B 5/00 | (2006.01) |
| A61H 1/00 | (2006.01) |
| A61N 1/365 | (2006.01) |
| A61B 5/01 | (2006.01) |
| A61B 5/0215 | (2006.01) |
| A61B 5/026 | (2006.01) |
| A61B 5/04 | (2006.01) |
| A61B 5/145 | (2006.01) |
| A61H 23/00 | (2006.01) |
| A61N 1/362 | (2006.01) |
| A61N 1/375 | (2006.01) |
| A61M 31/00 | (2006.01) |
| A61N 5/06 | (2006.01) |
| A61N 7/00 | (2006.01) |

(52) U.S. Cl.
CPC .......... *A61B 5/0031* (2013.01); *A61B 5/0084* (2013.01); *A61B 5/01* (2013.01); *A61B 5/026* (2013.01); *A61B 5/0215* (2013.01); *A61B 5/04* (2013.01); *A61B 5/14503* (2013.01); *A61B 5/14539* (2013.01); *A61B 5/14542* (2013.01); *A61B 5/686* (2013.01); *A61H 1/008* (2013.01); *A61H 23/004* (2013.01); *A61M 5/14276* (2013.01); *A61M 31/002* (2013.01); *A61N 1/056* (2013.01); *A61N 1/0534* (2013.01); *A61N 1/0551* (2013.01); *A61N 1/3601* (2013.01); *A61N 1/362* (2013.01); *A61N 1/3605* (2013.01); *A61N 1/365* (2013.01); *A61N 1/36125* (2013.01); *A61N 1/36139* (2013.01); *A61N 1/3756* (2013.01); *A61N 1/37211* (2013.01); *A61N 5/0601* (2013.01); *A61N 7/00* (2013.01); *A61B 2560/0219* (2013.01); *A61H 2201/1207* (2013.01); *A61M 2205/8206* (2013.01)

(56) References Cited

U.S. PATENT DOCUMENTS

| | | | |
|---|---|---|---|
| 5,828,340 | A | 10/1998 | Johnson |
| 5,861,019 | A | 1/1999 | Sun et al. |
| 6,051,017 | A | 4/2000 | Loeb et al. |
| 6,061,596 | A | 5/2000 | Richmond et al. |
| 6,175,764 | B1 | 1/2001 | Loeb |
| 6,185,455 | B1 | 2/2001 | Loeb |
| 6,201,453 | B1 | 3/2001 | Chan |
| 6,214,032 | B1 | 4/2001 | Loeb et al. |
| 6,360,750 | B1 | 3/2002 | Gerber et al. |
| 6,473,652 | B1 | 10/2002 | Sarwal et al. |
| 6,477,425 | B1 | 11/2002 | Nowick et al. |
| 6,505,074 | B2 | 1/2003 | Boveja et al. |
| 6,582,441 | B1 | 6/2003 | He et al. |
| 6,650,943 | B1 | 11/2003 | Whitehurst |
| 6,652,449 | B1 | 11/2003 | Gross et al. |
| 6,709,385 | B2 | 3/2004 | Forsell |
| 6,735,474 | B1 | 5/2004 | Loeb et al. |
| 6,836,684 | B1 | 12/2004 | Rijkhoff et al. |
| 6,953,429 | B2 | 10/2005 | Forsell et al. |
| 6,990,376 | B2 | 1/2006 | Tanaagho et al. |
| 7,027,860 | B2 | 4/2006 | Bruninga et al. |
| 7,054,689 | B1 | 5/2006 | Whitehurst et al. |
| 7,062,330 | B1 | 6/2006 | Boveja et al. |
| 7,142,925 | B1 | 11/2006 | Bhadra et al. |
| 7,191,007 | B2 | 3/2007 | Desai et al. |
| 7,295,879 | B2 | 11/2007 | Denker et al. |
| 7,330,756 | B2 | 2/2008 | Marnfeldt |
| 7,351,921 | B1 | 4/2008 | Haller |
| 7,499,753 | B2 | 3/2009 | Forsell |
| 7,580,752 | B2 | 8/2009 | Gerber et al. |
| 7,582,053 | B2 | 9/2009 | Gross et al. |
| 7,599,744 | B2 | 10/2009 | Giordano et al. |
| 7,621,863 | B2 | 11/2009 | Forsell |
| 7,643,880 | B2 | 1/2010 | Tanagho et al. |
| 7,647,112 | B2 | 1/2010 | Tracey et al. |
| 7,706,892 | B2 | 4/2010 | Colvin et al. |
| 7,763,034 | B2 | 7/2010 | Siegel et al. |
| 7,781,683 | B2 | 8/2010 | Haller et al. |
| 7,857,819 | B2 | 12/2010 | Jaax et al. |
| 7,881,803 | B2 | 2/2011 | Parramon et al. |
| 7,908,014 | B2 | 3/2011 | Schulman et al. |
| 7,979,126 | B2 | 7/2011 | Payne et al. |
| 7,979,140 | B2 | 7/2011 | Schulman |
| 8,019,419 | B1 | 9/2011 | Panescu et al. |
| 8,019,423 | B2 | 9/2011 | Possover |
| 8,055,336 | B1 | 11/2011 | Schulman et al. |
| 8,096,939 | B2 | 1/2012 | Forsell |
| 8,175,716 | B2 | 5/2012 | Rahman et al. |
| 8,214,048 | B1 | 7/2012 | Whitehurst et al. |
| 8,369,963 | B2 | 2/2013 | Parramon et al. |
| 8,386,048 | B2 | 2/2013 | McClure et al. |
| 8,401,663 | B2 | 3/2013 | Aghassian |
| 8,489,191 | B2 | 7/2013 | Possover |
| 8,494,658 | B2 | 7/2013 | Crowe et al. |
| 8,498,716 | B2 | 7/2013 | Chen et al. |
| 8,504,138 | B1 | 8/2013 | Pivonka et al. |
| 8,556,796 | B2 | 10/2013 | Forsell |
| 8,585,617 | B2 * | 11/2013 | Mashiach ............ A61B 5/0031 600/534 |
| 8,588,917 | B2 | 11/2013 | Whitehurst et al. |
| 8,624,787 | B2 | 1/2014 | Druyan et al. |
| 8,630,705 | B2 | 1/2014 | Mann et al. |
| 8,634,928 | B1 | 1/2014 | O'Driscoll et al. |
| 8,639,342 | B2 | 1/2014 | Possover |
| 8,655,451 | B2 | 2/2014 | Klosterman et al. |
| 8,666,491 | B2 | 3/2014 | Chen et al. |
| 8,774,912 | B2 | 7/2014 | Gerber |
| 8,836,172 | B2 * | 9/2014 | Hamam ............... H04B 5/0037 307/104 |
| 8,849,412 | B2 | 9/2014 | Perryman et al. |
| 8,862,241 | B2 | 10/2014 | Forsell |
| 8,874,217 | B2 | 10/2014 | Alataris et al. |
| 8,886,321 | B2 | 11/2014 | Rohrer et al. |
| 8,886,339 | B2 | 11/2014 | Faltys et al. |
| 8,892,214 | B2 | 11/2014 | Bonde et al. |
| 8,903,502 | B2 | 12/2014 | Perryman et al. |
| 8,909,343 | B2 | 12/2014 | Towe |
| 8,972,004 | B2 | 3/2015 | Simon et al. |
| 8,983,612 | B2 | 3/2015 | Fang et al. |
| 8,989,861 | B2 | 3/2015 | Su et al. |
| 9,020,602 | B2 | 4/2015 | Aghassian |
| 9,031,665 | B2 | 5/2015 | Aghassian |
| 9,042,997 | B2 | 5/2015 | Rahman et al. |
| 9,044,158 | B2 | 6/2015 | Varahramyan et al. |
| 9,072,904 | B2 | 7/2015 | Parramon et al. |
| 9,168,374 | B2 | 10/2015 | Su |
| 9,192,764 | B2 | 11/2015 | Rohrer et al. |
| 9,233,258 | B2 | 1/2016 | Simon et al. |
| 9,242,106 | B2 | 1/2016 | Klosterman et al. |
| 9,254,393 | B2 | 2/2016 | Perryman et al. |
| 9,289,607 | B2 | 3/2016 | Su et al. |
| 9,351,655 | B2 | 5/2016 | McDonald et al. |
| 9,351,664 | B2 | 5/2016 | Forsell |
| 9,352,150 | B2 | 5/2016 | Stevenson |
| 9,352,158 | B2 | 5/2016 | Lee et al. |
| 9,352,162 | B2 | 5/2016 | Lamont et al. |
| D758,596 | S | 6/2016 | Perryman et al. |

(56) References Cited

U.S. PATENT DOCUMENTS

| | | |
|---|---|---|
| 9,357,949 B2 | 6/2016 | Drew |
| 9,358,381 B2 | 6/2016 | Smon |
| 9,358,383 B2 | 6/2016 | Boyd et al. |
| 9,358,390 B2 | 6/2016 | Polefko et al. |
| 9,358,391 B2 | 6/2016 | Zhu et al. |
| 9,358,392 B2 | 6/2016 | Mashiach |
| 9,358,394 B2 | 6/2016 | Steinke et al. |
| 9,358,395 B2 | 6/2016 | Tweden et al. |
| 9,358,396 B2 | 6/2016 | Holley |
| 9,358,398 B2 | 6/2016 | Moffitt et al. |
| 9,358,399 B2 | 6/2016 | Carbunaru et al. |
| 9,359,449 B2 | 6/2016 | Deisseroth et al. |
| 9,364,658 B2 | 6/2016 | Wechter |
| 9,364,666 B2 | 6/2016 | Chen |
| 9,364,667 B1 | 6/2016 | Dinsmoor et al. |
| 9,364,668 B2 | 6/2016 | Marsh |
| 9,364,672 B2 | 6/2016 | Marnfeldt |
| 9,364,673 B2 | 6/2016 | Lamont et al. |
| 9,364,678 B2 | 6/2016 | Atanasoska et al. |
| 9,364,679 B2 | 6/2016 | John |
| 9,365,628 B2 | 6/2016 | Deisseroth et al. |
| 9,366,871 B2 | 6/2016 | Ghosh et al. |
| 9,368,710 B2 | 6/2016 | Wang et al. |
| 9,370,664 B2 | 6/2016 | Marnfeldt et al. |
| 9,375,563 B2 | 6/2016 | Govea |
| 9,375,567 B2 | 6/2016 | Fell |
| 9,375,571 B2 | 6/2016 | Errico et al. |
| 9,375,574 B2 | 6/2016 | Kaula et al. |
| 9,375,575 B2 | 6/2016 | Moffitt et al. |
| 9,381,342 B2 | 7/2016 | Barker |
| 9,381,346 B2 | 7/2016 | Lee et al. |
| 9,381,359 B2 | 7/2016 | Parramon et al. |
| 9,381,360 B2 | 7/2016 | Hershey |
| 9,381,364 B2 | 7/2016 | Rahman et al. |
| 9,381,367 B2 | 7/2016 | Janzig |
| 9,387,322 B2 | 7/2016 | Bhadra et al. |
| 9,387,326 B2 | 7/2016 | Moffitt |
| 9,387,327 B2 | 7/2016 | Alataris et al. |
| 9,387,328 B2 | 7/2016 | Lee |
| 9,387,334 B2 | 7/2016 | Lee et al. |
| 9,387,338 B2 | 7/2016 | Burnett |
| 9,392,955 B2 | 7/2016 | Folkerts et al. |
| 9,393,396 B2 | 7/2016 | Peyman |
| 9,393,421 B2 | 7/2016 | Carbunaru et al. |
| 9,393,422 B2 | 7/2016 | Moffitt et al. |
| 9,393,423 B2 | 7/2016 | Parramon et al. |
| 9,393,433 B2 | 7/2016 | Parramon et al. |
| 9,393,435 B2 | 7/2016 | Mashiach |
| 9,394,347 B2 | 7/2016 | Deisseroth et al. |
| 9,397,639 B2 | 7/2016 | Feldman et al. |
| 9,398,901 B2 | 7/2016 | Tischendorf et al. |
| 9,399,130 B2 | 7/2016 | Bonde et al. |
| 9,399,131 B2 | 7/2016 | DiGiore et al. |
| 9,399,132 B2 | 7/2016 | Parramon et al. |
| 9,399,134 B2 | 7/2016 | Simon et al. |
| 9,401,625 B2 | 7/2016 | Zottola et al. |
| 2002/0055779 A1 | 5/2002 | Andrews |
| 2003/0009201 A1 | 1/2003 | Forsell |
| 2003/0169207 A1 | 9/2003 | Beigel |
| 2004/0049240 A1 | 3/2004 | Gerber et al. |
| 2004/0055610 A1 | 3/2004 | Forsell |
| 2004/0138725 A1 | 7/2004 | Forsell |
| 2004/0193229 A1 | 9/2004 | Starkebaum et al. |
| 2004/0250820 A1 | 12/2004 | Forsell |
| 2005/0055063 A1 | 3/2005 | Loeb et al. |
| 2005/0113878 A1 | 5/2005 | Gerber |
| 2005/0283202 A1 | 12/2005 | Gellman |
| 2006/0149333 A1 | 7/2006 | Tanagho et al. |
| 2006/0155347 A1 | 7/2006 | Forsell |
| 2006/0161204 A1 | 7/2006 | Colvin et al. |
| 2006/0161225 A1 | 7/2006 | Sormann et al. |
| 2007/0055324 A1 | 3/2007 | Thompson et al. |
| 2007/0060955 A1 | 3/2007 | Strother et al. |
| 2007/0191908 A1 | 8/2007 | Jacob et al. |
| 2007/0282378 A1 | 12/2007 | Huang et al. |
| 2008/0039904 A1 | 2/2008 | Bulkes et al. |
| 2008/0077184 A1 | 3/2008 | Denker et al. |
| 2008/0188917 A1 | 8/2008 | Gerber |
| 2008/0275524 A1 | 11/2008 | Furness et al. |
| 2009/0058361 A1 | 3/2009 | John |
| 2009/0069869 A1 | 3/2009 | Stouffer et al. |
| 2009/0157145 A1 | 6/2009 | Cauller |
| 2009/0247817 A1 | 10/2009 | Forsell |
| 2009/0254144 A1 | 10/2009 | Bhadra et al. |
| 2010/0241195 A1 | 9/2010 | Meadows et al. |
| 2010/0286734 A1 | 11/2010 | Yun et al. |
| 2010/0292629 A1 | 11/2010 | Dacey, Jr. et al. |
| 2011/0071590 A1 | 3/2011 | Mounaim et al. |
| 2011/0093036 A1 | 4/2011 | Mashiach |
| 2011/0172733 A1 | 7/2011 | Lima et al. |
| 2011/0245892 A1 | 10/2011 | Kast et al. |
| 2012/0010680 A1 | 1/2012 | Wei et al. |
| 2012/0095531 A1 | 4/2012 | Derbas et al. |
| 2012/0101874 A1 | 4/2012 | Ben-Haim et al. |
| 2012/0119698 A1 | 5/2012 | Karalis et al. |
| 2012/0136413 A1 | 5/2012 | Bonde et al. |
| 2012/0197342 A1 | 8/2012 | Towe |
| 2012/0203215 A1 | 8/2012 | Riedel et al. |
| 2012/0203218 A1 | 8/2012 | Bonn |
| 2012/0203306 A1 | 8/2012 | Sarvazyan et al. |
| 2012/0235502 A1* | 9/2012 | Kesler ............... H03H 7/40 307/104 |
| 2012/0283800 A1 | 11/2012 | Perryman et al. |
| 2012/0316622 A1 | 12/2012 | Whitehurst et al. |
| 2013/0053767 A1 | 2/2013 | Pivonka et al. |
| 2013/0066400 A1 | 3/2013 | Perryman et al. |
| 2013/0110201 A1 | 5/2013 | Bonde et al. |
| 2013/0165996 A1 | 6/2013 | Meadows et al. |
| 2013/0181517 A1 | 7/2013 | Maguire et al. |
| 2013/0215979 A1 | 8/2013 | Yakovlev et al. |
| 2013/0261692 A1 | 10/2013 | Cardinal et al. |
| 2013/0274829 A1 | 10/2013 | Gupta et al. |
| 2013/0289446 A1 | 10/2013 | Stone et al. |
| 2013/0289647 A1 | 10/2013 | Bhadra et al. |
| 2014/0163580 A1 | 6/2014 | Tischendorf et al. |
| 2014/0163644 A1 | 6/2014 | Scott et al. |
| 2014/0180365 A1 | 6/2014 | Perryman et al. |
| 2014/0257268 A1 | 9/2014 | Sachs et al. |
| 2014/0350041 A1 | 11/2014 | Yun et al. |
| 2014/0350633 A1 | 11/2014 | Gustafson et al. |
| 2015/0134026 A1 | 5/2015 | Kaula et al. |
| 2015/0134028 A1 | 5/2015 | Kaula et al. |
| 2015/0157389 A1 | 6/2015 | Ben-Ezra et al. |
| 2015/0196164 A1 | 7/2015 | Waylor et al. |
| 2015/0224323 A1 | 8/2015 | Chen et al. |
| 2015/0249344 A1 | 9/2015 | Poon et al. |
| 2015/0321017 A1 | 11/2015 | Perryman et al. |
| 2015/0335285 A1 | 11/2015 | Poon et al. |
| 2016/0023003 A1 | 1/2016 | Perryman et al. |
| 2016/0023005 A1 | 1/2016 | Perryman et al. |
| 2016/0151628 A1 | 6/2016 | Simon et al. |
| 2016/0151633 A1 | 6/2016 | Goetz et al. |
| 2016/0151639 A1 | 6/2016 | Scharf et al. |
| 2016/0158051 A1 | 6/2016 | Mische |
| 2016/0158542 A1 | 6/2016 | Ahmed |
| 2016/0158549 A1 | 6/2016 | Woods et al. |
| 2016/0158553 A1 | 6/2016 | Panken et al. |
| 2016/0158558 A1 | 6/2016 | Shanahan et al. |
| 2016/0158564 A1 | 6/2016 | Rao et al. |
| 2016/0158565 A1 | 6/2016 | Lee |
| 2016/0158566 A1 | 6/2016 | Thacker et al. |
| 2016/0166203 A1 | 6/2016 | Goldstein |
| 2016/0166326 A1 | 6/2016 | Bakker et al. |
| 2016/0166829 A1 | 6/2016 | Pianca et al. |
| 2016/0166833 A1 | 6/2016 | Oh et al. |
| 2016/0166841 A1 | 6/2016 | Ostroff |
| 2016/0175583 A1 | 6/2016 | Kveen et al. |
| 2016/0175607 A1 | 6/2016 | Deisseroth et al. |
| 2016/0183842 A1 | 6/2016 | Najafi |
| 2016/0184179 A1 | 6/2016 | Asfora |
| 2016/0184591 A1 | 6/2016 | Feldman et al. |
| 2016/0184592 A1 | 6/2016 | Marnfeldt et al. |
| 2016/0184597 A1 | 6/2016 | Andresen et al. |
| 2016/0190698 A1 | 6/2016 | Andresen et al. |

(56) References Cited

U.S. PATENT DOCUMENTS

| | | |
|---|---|---|
| 2016/0193466 A1 | 7/2016 | Burnett |
| 2016/0193469 A1 | 7/2016 | Cardinal et al. |
| 2016/0193472 A1 | 7/2016 | Ozawa et al. |
| 2016/0199096 A1 | 7/2016 | Gardanier et al. |
| 2016/0199657 A1 | 7/2016 | Jiang et al. |
| 2016/0199658 A1 | 7/2016 | Nassif et al. |
| 2016/0199659 A1 | 7/2016 | Jiang et al. |
| 2016/0199660 A1 | 7/2016 | Rao et al. |
| 2016/0203187 A1 | 7/2016 | Alonso et al. |
| 2016/0206457 A1 | 7/2016 | Wong et al. |
| 2016/0206876 A1 | 7/2016 | Rajguru et al. |
| 2016/0206881 A1 | 7/2016 | Libbus |
| 2016/0213914 A1 | 7/2016 | He et al. |
| 2016/0213930 A1 | 7/2016 | Walker et al. |
| 2016/0213932 A1 | 7/2016 | Lee |
| 2016/0216768 A1 | 7/2016 | Goetz et al. |
| 2016/0216769 A1 | 7/2016 | Goetz et al. |
| 2016/0303385 A1 | 10/2016 | Poon et al. |
| 2016/0303386 A1 | 10/2016 | Poon et al. |
| 2016/0336813 A1 | 11/2016 | Yeh et al. |
| 2016/0339256 A1 | 11/2016 | Poon et al. |
| 2016/0344238 A1 | 11/2016 | Yeh et al. |
| 2016/0344240 A1 | 11/2016 | Yeh et al. |

FOREIGN PATENT DOCUMENTS

| | | |
|---|---|---|
| EP | 1362614 A1 | 11/2003 |
| EP | 1121046 B1 | 10/2004 |
| EP | 0802816 B1 | 5/2005 |
| EP | 1119314 B1 | 6/2006 |
| EP | 1600193 B1 | 8/2006 |
| EP | 1587463 B1 | 3/2007 |
| EP | 1587464 B1 | 8/2007 |
| EP | 1587465 B1 | 11/2007 |
| EP | 1217972 B1 | 12/2007 |
| EP | 1545702 B1 | 2/2008 |
| EP | 1911490 A1 | 4/2008 |
| EP | 1545695 B1 | 8/2008 |
| EP | 1702587 B1 | 12/2008 |
| EP | 1171190 B1 | 5/2011 |
| EP | 2247338 B1 | 8/2012 |
| EP | 2389975 B1 | 8/2012 |
| EP | 1904173 B8 | 12/2015 |
| EP | 2155062 B1 | 6/2016 |
| EP | 2211977 B1 | 6/2016 |
| EP | 2498872 B1 | 6/2016 |
| EP | 2914169 A4 | 6/2016 |
| EP | 3024540 A1 | 6/2016 |
| EP | 3030310 A1 | 6/2016 |
| EP | 3033147 A1 | 6/2016 |
| EP | 3037129 A1 | 6/2016 |
| EP | 2016083443 A1 | 6/2016 |
| EP | 2016090175 A1 | 6/2016 |
| EP | 2016090196 A1 | 6/2016 |
| EP | 2167189 B1 | 7/2016 |
| EP | 2185239 B1 | 7/2016 |
| EP | 2370172 B1 | 7/2016 |
| EP | 2658606 B1 | 7/2016 |
| EP | 2734268 B1 | 7/2016 |
| EP | 3038704 A1 | 7/2016 |
| EP | 3041565 A1 | 7/2016 |
| EP | 3041566 A1 | 7/2016 |
| EP | 3041567 A1 | 7/2016 |
| EP | 3041570 A1 | 7/2016 |
| EP | 3041571 A1 | 7/2016 |
| EP | 3042695 A1 | 7/2016 |
| EP | 3046621 | 7/2016 |
| EP | 3046621 A1 | 7/2016 |
| EP | 3047874 A1 | 7/2016 |
| JP | 2016538090 A | 12/2016 |
| WO | WO-0066220 A1 | 11/2000 |
| WO | WO-2008080073 A2 | 7/2008 |
| WO | WO-2011150430 A2 | 12/2011 |
| WO | WO-2014071079 A1 | 5/2014 |
| WO | WO-2014205407 A2 | 12/2014 |
| WO | WO-2015039108 A2 | 3/2015 |
| WO | WO-2015039108 A3 | 3/2015 |
| WO | WO-2015196164 A2 | 6/2015 |
| WO | WO-2015139053 A1 | 9/2015 |
| WO | WO-2015179225 A1 | 11/2015 |
| WO | WO-2016028608 A1 | 2/2016 |
| WO | WO-2016029159 A2 | 2/2016 |
| WO | WO-2016083460 A1 | 6/2016 |
| WO | WO-2016083465 A1 | 6/2016 |
| WO | WO-2016094269 A1 | 6/2016 |
| WO | WO-2016103245 A1 | 6/2016 |
| WO | WO-2016109833 A1 | 7/2016 |
| WO | WO-2016109836 A2 | 7/2016 |
| WO | WO-2016112398 A1 | 7/2016 |
| WO | WO-2016112401 A1 | 7/2016 |
| WO | WO-2016114923 A1 | 7/2016 |
| WO | WO-2016115031 A2 | 7/2016 |
| WO | WO-2016118943 A2 | 7/2016 |
| WO | WO-2016124000 A1 | 7/2016 |

OTHER PUBLICATIONS

"U.S. Appl. No. 15/208,108, Preliminary Amendment filed Aug. 5, 2016", 7 pgs.

"U.S. Appl. No. 15/208,155, Preliminary Amendment filed Aug. 5, 2016", 9 pgs.

"International Application Serial No, PCT/US2014/055885, International Preliminary Report on Patentability mailed Mar. 31, 2016", 9 pgs.

"International Application Serial No. PCT/US2015/030995, International Search Report mailed Oct. 16, 2015", 4 pgs.

"International Application Serial No. PCT/US2015/030995, Invitation to Pay Add'l Fees and Partial Search Rpt mailed Aug. 12, 2015", 2 pgs.

"International Application Serial No. PCT/US2015/030995, Written Opinion mailed Oct. 16, 2015", 6 pgs.

Aubert, Herve, "RFID Technology for Human Implant Devices Technologie RFID pour implants dans le corps humain", Comptes rendus àl'Académie des Sciences (Special issue on nanosciences/nanotechnologies), (Mar. 1, 2011), 18 pgs.

Kim, Sanghoek, et al., "MidfieldWireless Powering of Subwavelength Autonomous Devices", Physical Review Letters, vol. 110, (May 17, 2013), 203905-1-203905-5.

Occhiuzzi, Cecilia, et al., "Human Body Sensing: a Pervasive Approach by Implanted RFID Tags", 3rd International Symposium on Applied Sciences in Biomedical and Communication Technologies (ISABEL), (Jan. 28, 2011), 5 pgs.

Radiomm, Soheil, et al., "Far-field RF Powering System for RFID and Implantable Devices with Monolithically Integrated On-Chip Antenna", IEEE Radio Frequency Integrated Circuits Symposium (RFIC), (Jun. 3, 2010), 4 pgs.

Thomas, Stewart, et al., "Modulated backscatter for ultra-low power uplinks from wearable and implantable devices", MedCOMM '12 Proceedings of the 2012 ACM workshop on Medical communication systems, (2012), 1-6.

Yeager, Daniel, et al., "A 9 UA, Addressable Gen2 Sensor Tag for Biosignal Acquisition", IEEE Journal of Solid-State Circuits, 45(10), (Oct. 2010), 2198-2209.

"International Application Serial No. PCT/US2014/055885, International Search Report mailed Mar. 5, 2015", 5 pgs.

"International Application Serial No. PCT/US2014/055885, Written Opinion mailed Mar. 5, 2015", 7 pgs.

Ho, JS, et al., "Midfield Wireless Powering for Implantable Systems", Proceedings of the IEEE. vol. 101, No. 6, [Online] retrieved from the internet: <URL:http://web.stanford.edu/group/poongroup/cgi-bin/wordpress/wp-content/uploads/2013/05/PIEEE%202013%20Ho.pdf>, (Apr. 4, 2013), 1-10.

Park, Si, et al., "Enhancement of wireless power transmission into biological tissues using a high surface impedance ground plane", Progress in Electromagnetics Research. vol. 135, [Online] retrieved from the internet: <URL:http://onlinewww.jpier.org/PIER/pier135/08.12110902.pdf>, (Dec. 12, 2012), 123-136.

"U.S. Appl. No. 15/196,814, First Action Interview—Office Action Summary mailed Oct. 17, 2016", 5 pgs.

(56) References Cited

OTHER PUBLICATIONS

"U.S. Appl. No. 15/196,814, Response filed Nov. 14, 2016 to First Action Interview—Office Action Summary mailed Oct. 17, 2016", 10 pgs.
"U.S. Appl. No, 15/196,874, First Action Interview—Office Action Summary mailed Oct. 17, 2016", Examiner Interview Summary from Oct. 17, 2016 included, 5 pgs.
"U.S. Appl. No. 15/200,543, Notice of Allowance mailed Oct. 14, 2016", 9 pgs.
"U.S. Appl. No. 15/208,155, Corrected Notice of Allowance mailed Nov. 10, 2016", 2 pgs.
"U.S. Appl. No. 15/196,991, Response Filed Dec. 19, 2016 to First Action Interview—Pre-Interview Communication mailed Sep. 1, 2016", 13 pgs.
"European Application Serial No. 14843943.3, Preliminary Amendment filed Dec. 1, 2016", 12 pgs.
U.S. Appl. No. 15/196,814, filed Jun. 29, 2016, Multi-Element Coupler for Generation of Electromagnetic Energy.
U.S. Appl. No. 15/196,874, filed Jun. 29, 2016, Multi-Element Coupler for Generation of Electromagnetic Energy.
U.S. Appl. No. 15/196,991, filed Jun. 29, 2016, Multi-Element Coupler for Generation of Electromagnetic Energy.
U.S. Appl. No. 15/200,543, filed Jul. 1, 2016, Midfield Coupler.
U.S. Appl. No. 15/208.108, filed Jul. 12, 2016, Midfield Coupler.
U.S. Appl. No. 15/208,155, filed Jul. 12, 2016, Midfield Coupler.
"U.S. Appl. No. 13/734,772, File History from Jan. 4, 2013 to Jan. 4, 2016", 213 pgs.
"U.S. Appl. No. 14/424,303, Preliminary Amendment filed Jan. 14, 2016", 4 pgs.
"U.S. Appl. No. 15/196,814, First Action Interview—Pre-Interview Communication mailed Sep. 8, 2016", 4 pgs.
"U.S. Appl. No. 15/196,874, First Action Interview—Pre-Interview Communication mailed Sep. 8, 2016", 4 pgs.
"U.S. Appl. No. 15/196,991, First Action Interview—Pre-Interview Communication mailed Sep. 1, 2016", 5 pgs.
"U.S. Appl. No. 15/208,155, Notice of Allowance mailed Sep. 26, 2016", 17 pgs.
"Claims of U.S. Appl. No. 15/200,543 as filed on Aug. 4, 2016".
"International Application Serial No. PCT/US2014/055885, Invitation to Pay Additional fees mailed Jan. 5, 2015", 2 pgs.
Giamalaki, M. I, et al., "Focused microwave radiometry from a possible functional imaging perspective: theoretical optimization of the properties of a microwave radiometry system", Journal of Instrumentation 4(05), (May 2009), 8 pgs.
Ho, John S, et al., "MidfieldWireless Powering for Implantable Systems", Proceedings of the IEEE; 101(6), (Jun. 2013), 1369-1378.
Ho, John S, "Planar immersion lens with metasurfaces", Physical Review B, vol. 91, (Mar. 30, 2015), 11 pgs.
Ho, John S, et al., "Wireless power transfer to deep-tissue microimplants", Proceedings of the National Academy of Sciences of the United States of America; 111(22), (Jun. 3, 2014), 7974-7979.
Khaleghi, Ali, et al., "On the Use of a Dielectric Matching Layer for Ultra Wideband Medical Applications", Proceedings of the 7th International Conference on Body Area Networks, (Feb. 2012), 8 pgs.
Maccarini, Paolo, "Modeling the detectability of vesicoureteral reflux using microwave radiometry", Journal of Physics in Medicine and Biology; 55(18), (Sep. 2010), 5417-5435.
"European Application Serial No. 14843943.3, Extended European Search Report mailed Feb. 24, 2017", 9 pgs.

\* cited by examiner

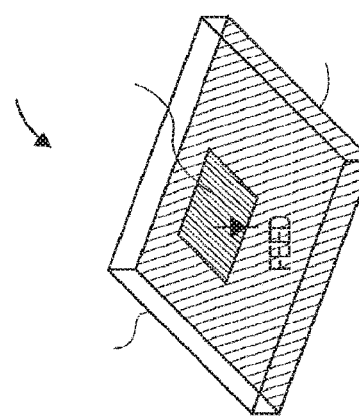 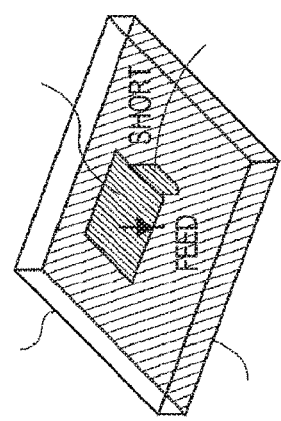 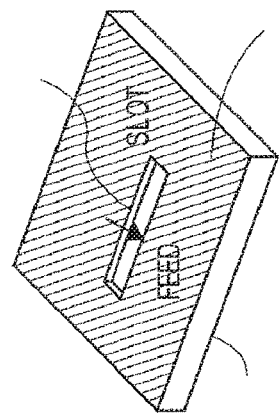
FIG. 1C  FIG. 1D  FIG. 1E
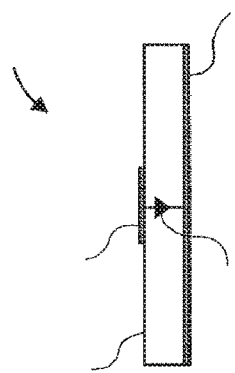 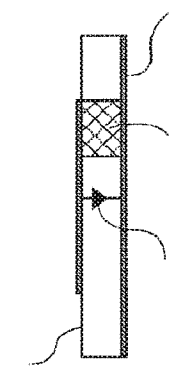 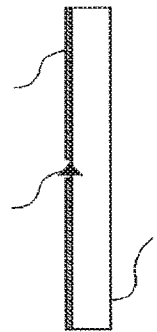
FIG. 1F  FIG. 1G  FIG. 1H

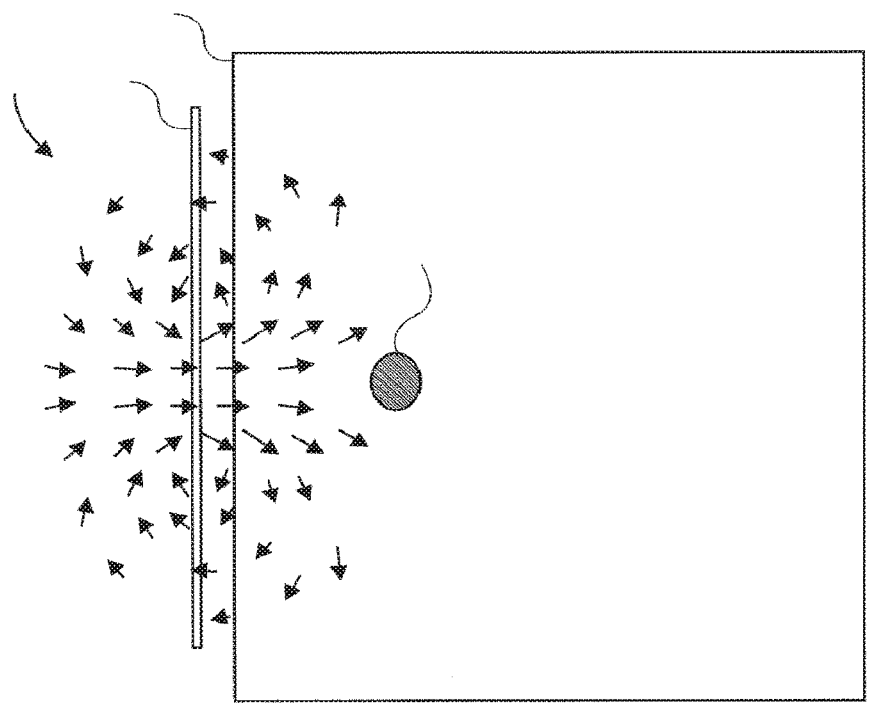
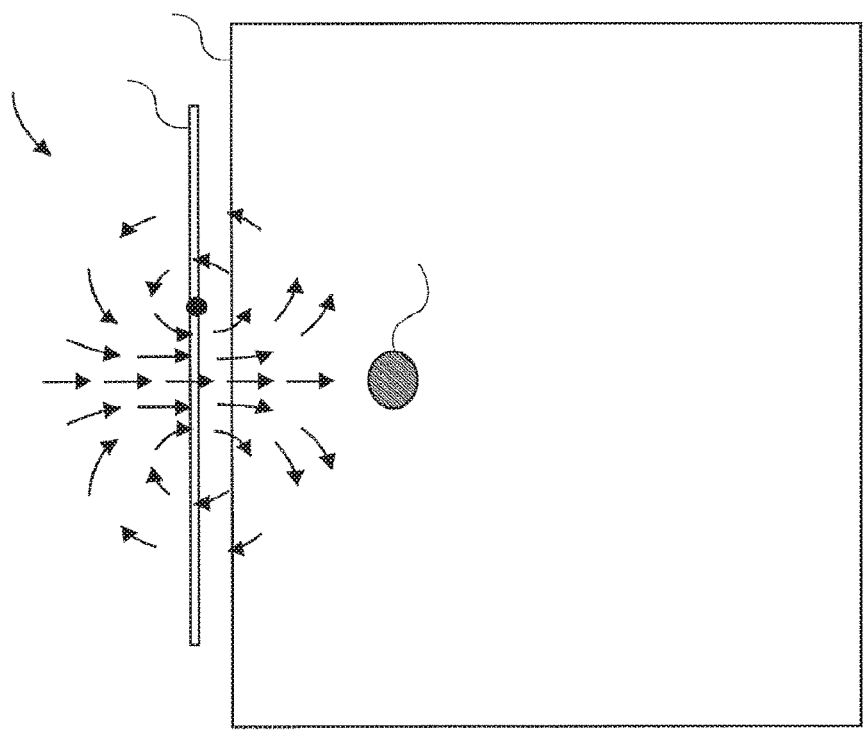
FIG. 2

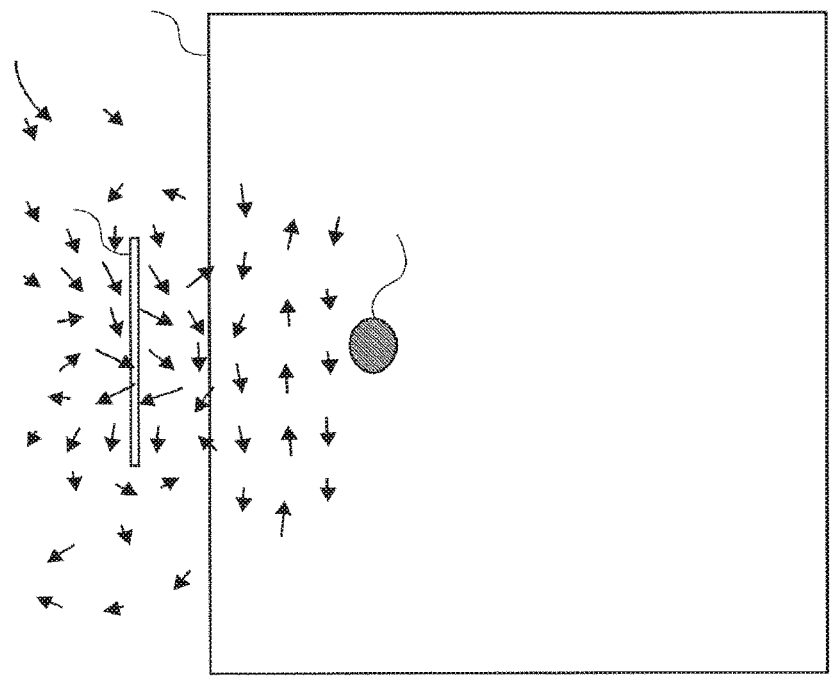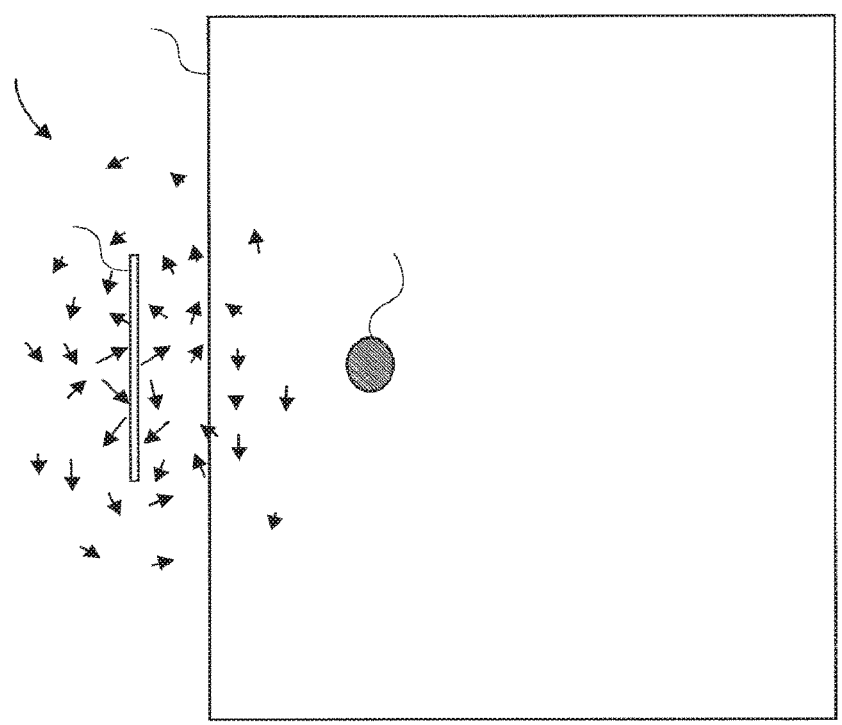
FIG. 3C

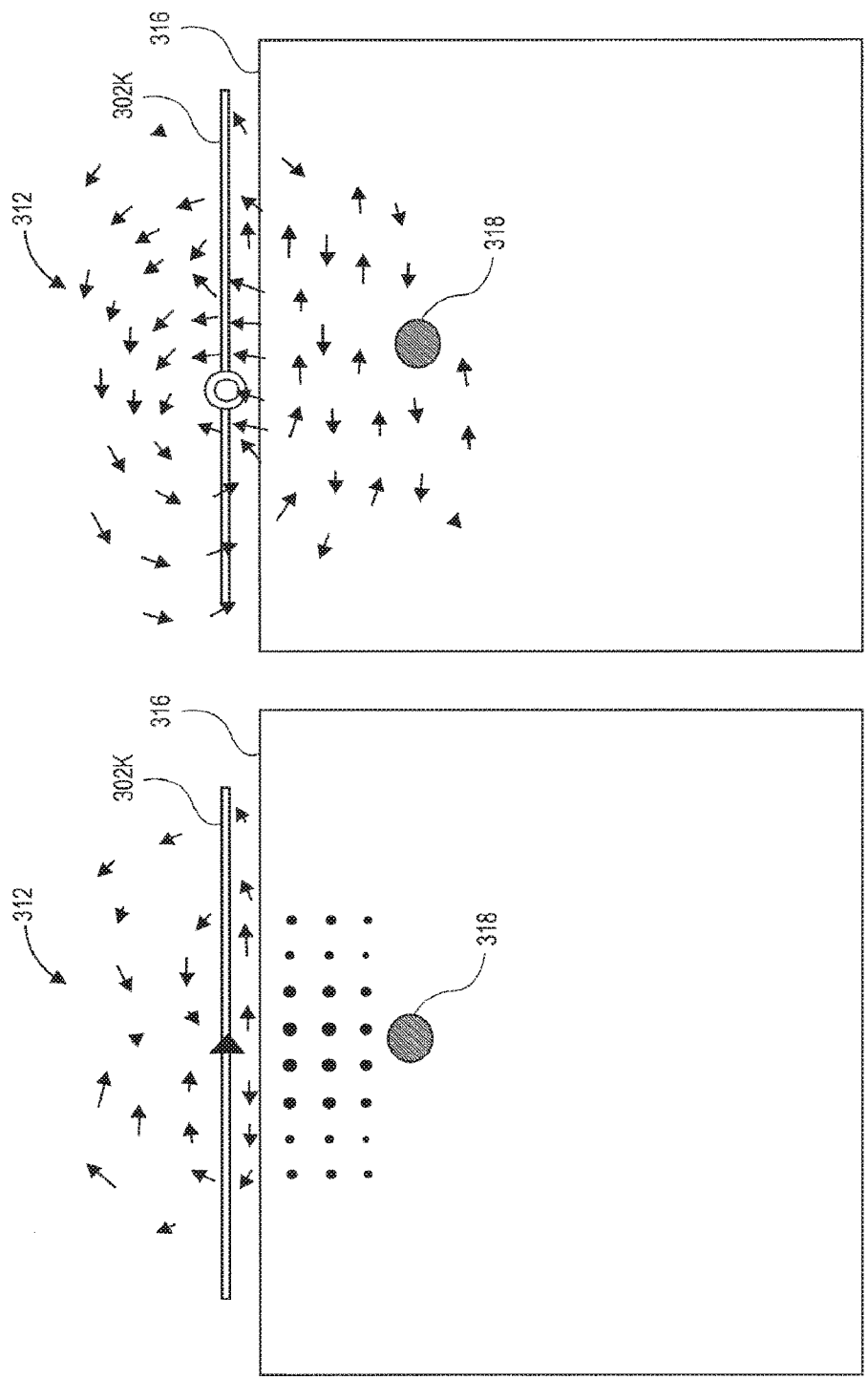

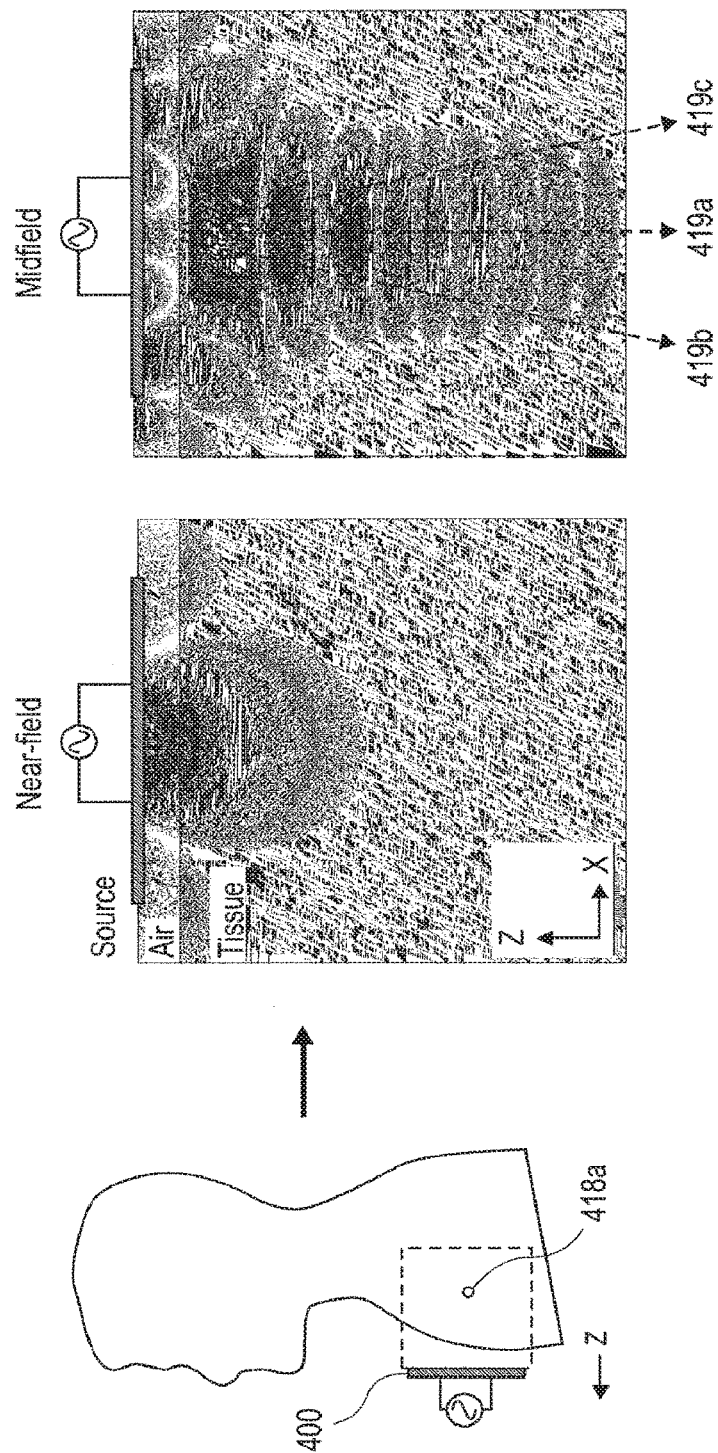

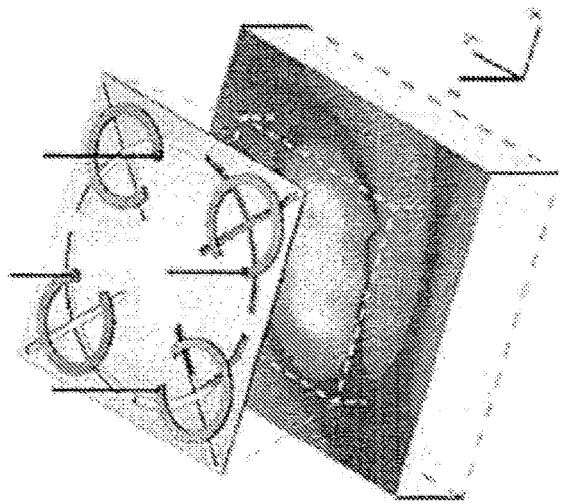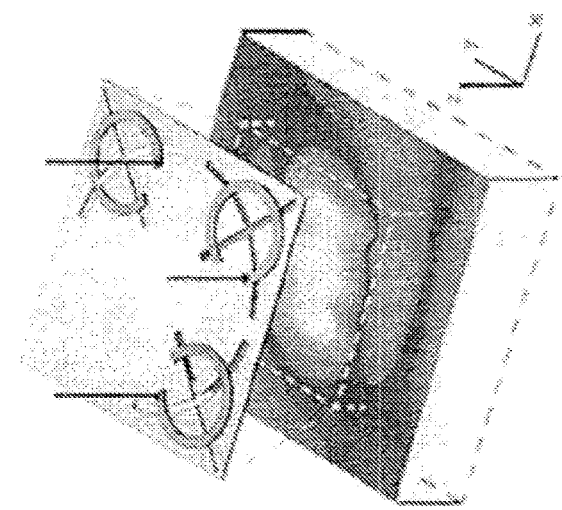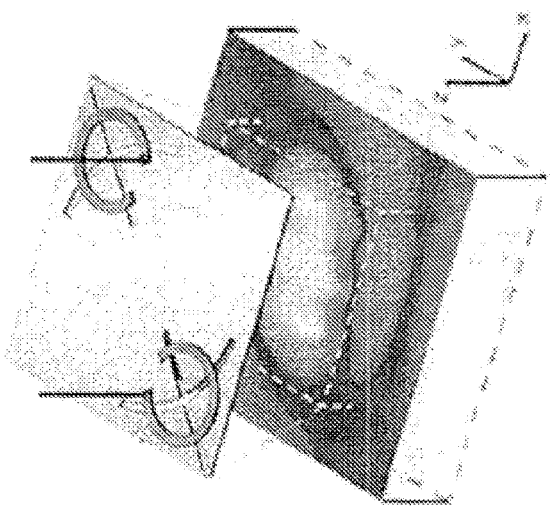
FIG. 8

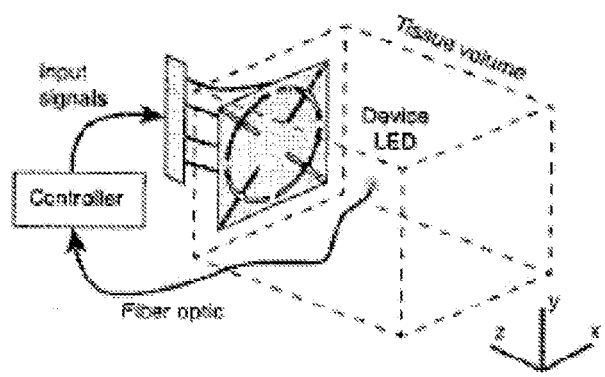
FIG. 10D
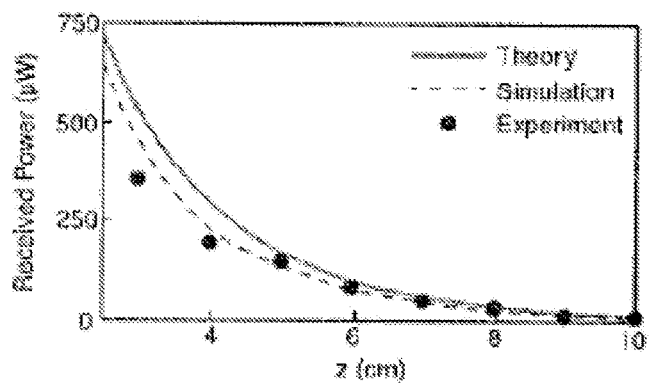
FIG. 10E
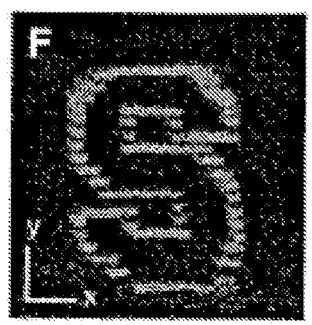 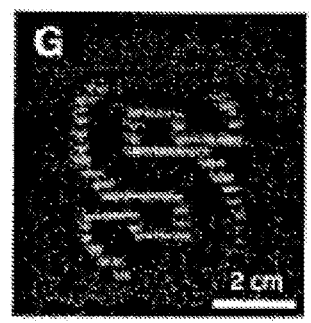
FIG. 10F          FIG. 10G Fabrication process and power consumption of selected integrated electronics

| Function | Fabrication Process | Power Consumption |
|---|---|---|
| Neural local field potential sensing (32) | 0.8 μm CMOS | 4.5 μW per channel |
| Optogenetic stimulation (33) | 0.8 μm HV CMOS | 400 μW |
| Neural recording (34) | 0.18 μm CMOS | 0.73 μW per channel |
| Pacemaker (24) | 0.5 μm CMOS | 8 μW |
| Intracardiac impedance measurement (35) | 0.18 μm CMOS | 6.67 μW per channel |
| Fluorimeter (36) | 0.6 μm CMOS | < 1 μJ per measurement |
| Intraocular pressure sensor (37) | 0.18 μm CMOS | 1.44 μJ per measurement |
| Temperature sensor (38) | 0.16 μm CMOS | 0.027 μJ per measurement |
| CMOS image sensor (39) | 0.18 μm CMOS | 3.4 μJ per frame |
| Locomotion (31) | 65 nm CMOS | 250 μW at 0.53 cm/s |

FIG. 16

MULTI-ELEMENT COUPLER FOR GENERATION OF ELECTROMAGNETIC ENERGY

CROSS REFERENCE TO RELATED APPLICATIONS

This application is a U.S. National Stage Filing under 35 U.S.C. 371 from International Application No. PCT/US2014/055885, filed Sep. 16, 2014, titled "Multi-Element Coupler for Generation of Electromagnetic Energy", which application claims the benefit of U.S. Provisional Appln. No. 61/878,436, filed Sep. 16, 2013, titled "Multi-Element Coupler", and U.S. Provisional Appln. No. 61/913,164, filed Dec. 6, 2013, titled "Power Management and Conversion for Medical Implants", all of which are incorporated herein by reference.

INCORPORATION BY REFERENCE

All publications and patent applications mentioned in this specification are herein incorporated by reference to the same extent as if each individual publication or patent application was specifically and individually indicated to be incorporated by reference.

FIELD

This disclosure is related generally to wireless power transfer. More specifically, this disclosure relates to delivering wireless power through tissue into a device implanted in a human or animal.

BACKGROUND

Systems and methods that supply power without electrical wiring are sometimes referred to as wireless energy transmission (WET). Wireless energy transmission greatly expands the types of applications for electrically powered devices. Implantable medical devices typically require an internal power source able to supply adequate power for the reasonable lifetime of the device or an electrical cable that traverses the skin.

More recently there has been an emphasis on systems that supply power to an implanted device without using transcutaneous wiring, sometimes referred to as a Transcutaneous Energy Transfer System (TETS). Frequently energy transfer is accomplished using two magnetically coupled coils set up like a transformer so power is transferred magnetically across the skin. Conventional systems are relatively sensitive to variations in position and alignment of the coils, typically requiring the coils to be physically close together and well aligned.

Existing systems that transmit power wirelessly based on magnetic fields typically operate in the near-field only, where the separation of the transmitter and receiver coils is less than or equal to the dimension of the coils.

Wireless powering has long been of interest for enhancing the function of implantable electronics, beginning in the early 1960's with experiments in transporting electromagnetic energy across the chest wall. Drawing conceptually on schemes for transferring power over air through objects coupled in the near-field, early manifestations involved bulky coils tether to vacuum tube power supplies or battery cells that posed severe challenges for long-term operation in the body. Advances in semiconductor technology have since enabled sophisticated devices that incorporate sensing and stimulation capabilities within cellular-scale dimensions. Nearly all existing systems, however, continue to require large structures for energy storage or harvesting, often several centimeters in the largest dimension with overall size, weight, and efficiency characteristics that constrain opportunities for integration into the body.

Near-field approaches rely on strong coupling occurring between objects with matched electrical characteristics, such as resonances and impedances. These near-field approaches do not generalize easily to geometries with extreme size asymmetry, while far-field transfer is limited by absorption over surfaces of the body.

The present disclosure describes methods and apparatus for wireless power transfer that overcome the limitations of previous wireless power transfer methods. The present disclosure provides a mid-field approach in which both evanescent and radiative components of a structure are coupled to modes in tissue that transport energy continuously away from the source. Interference resulting from phase differences between these components affords additional opportunity for spatially focused and dynamically adjustable field patterns inside tissue. The level of performance obtainable from the approach described in this disclosure can exceed requirements for advanced monitoring and control capabilities for applications in medicine, neuroscience, or human-machine interfaces.

SUMMARY

In one embodiment, a wireless power system is provided, comprising an external module having one or more sub-wavelength structures configured to transmit wireless power by manipulating evanescent fields outside of tissue to generate propagating fields inside the patient's tissue and thereby generate a spatially focused field in tissue, and an implantable
module configured to receive the wireless power from the external module, the implantable module including at least one sensor or stimulator configured to sense a parameter of the tissue or apply stimulation to the tissue.

In some embodiments, the at least one sensor is selected from the group consisting of a thermal sensor, a chemical sensor, a pressure sensor, and oxygen sensor, a PH sensor, a flow sensor, an electrical sensor, a strain sensor, a magnetic sensor, and an imaging sensor.

In other embodiments, the at least one stimulator is selected from the group consisting of an electrical stimulator, an optical stimulator, a chemical stimulator, and a mechanical stimulator.

In one embodiment, the implantable device comprises a modular design that allows interchangeable sensors and/or stimulators.

In some embodiments, the one or more sub-wavelength structures are selected from the group consisting of a patch, a PIFA, a slot in a ground plane, a cross slot in a ground plane, an aperture coupled circular slot in a ground plane, and a half slot in a ground plane.

In another embodiment, the external module further comprises one or more excitation ports coupled to the one or more sub-wavelength structures, at least one voltage source coupled to the one or more excitation ports, and a controller configured to adjust a phase and/or an amplitude delivered to the one or more sub-wavelength structures to adjust a position of a focal point of the spatially focused field in the tissue.

In one embodiment, the controller is configured to detect a power level of received wireless energy from the implanted module, and is configured to provide feedback to automatically adjust the position of the focal point to optimize wireless power transmission.

In another embodiment, the implantable module is configured to be implanted on, in, or near a heart to apply leadless pacing to the heart.

In some embodiments, the implantable module is configured to be implanted on, in, or near a brain to apply deep brain stimulation to the brain. In another embodiment, the implantable module is configured to be implanted on, in, or near a spinal cord to apply stimulation to the spinal cord. In yet another embodiment, the implantable module is configured to be implanted on, in, or near a muscular tissue of the tongue to apply stimulation to the tongue to treat obstructive sleep apnea.

A method of providing therapy to a patient is provided, comprising implanting a wireless power receiving in the patient, transmitting a mid-field propagating wave to the wireless power receiving module to power the module, sensing a parameter of the patient with the wireless power receiving module, and providing a therapy to the patient with the wireless power receiving module based on the sensed parameter.

In some embodiments, the transmitting step further comprises manipulating evanescent fields outside of the patient's tissue to generate propagating fields inside the patient's tissue and thereby generate a spatially focused field in the tissue.

A method of cardiac pacing in a patient is also provided, comprising implanting a wireless power receiving module in, on, or near a heart, transmitting a mid-field propagating wave to the wireless power receiving module to power the module, sensing a parameter of the heart with the wireless power receiving module, and providing electrical pacing to the heart with the wireless power receiving module based on the sensed parameter.

In some embodiments, the transmitting step further comprises manipulating evanescent fields outside of the patient's tissue to generate propagating fields inside the patient's tissue and thereby generate a spatially focused field in the tissue.

A method of deep brain stimulation is also provided, comprising implanting a wireless power receiving module in, on, or near a brain, transmitting a mid-field propagating wave to the wireless power receiving module to power the module, sensing a parameter of the brain with the wireless power receiving module, and providing stimulation to the brain with the wireless power receiving module based on the sensed parameter.

In some embodiments, the transmitting step further comprises manipulating evanescent fields outside of the patient's tissue to generate propagating fields inside the patient's tissue and thereby generate a spatially focused field in the tissue.

A method of stimulating tissue is provided, comprising implanting a wireless power receiving module into tissue, transmitting a mid-field propagating wave to the wireless power receiving module to power the module, sensing a parameter of the tissue with the wireless power receiving module, and providing stimulation to the tissue with the wireless power receiving module based on the sensed parameter.

In some embodiments, the transmitting step further comprises manipulating evanescent fields outside of the patient's tissue to generate propagating fields inside the patient's tissue and thereby generate a spatially focused field in the tissue.

In another embodiment, the method further comprises adjusting a focal point of the propagating wave to optimize wireless power transmission to the module.

In another embodiment, the transmitting step comprises transmitting the wave with a sub-wavelength structure that produces a magnetic field perpendicular to the wave and parallel to a tissue interface.

An apparatus configured to transfer wireless power through tissue is provided, comprising a substrate, at least one sub-wavelength structure disposed on the substrate, at least one radio-frequency port coupled to the at least one sub-wavelength structure, a voltage or current source coupled to the at least one radio-frequency port, and a controller configured to manage excitation of the at least one radio-frequency port and sub-wavelength structure with the voltage or current source to manipulate evanescent fields outside of tissue to generate propagating fields inside the tissue and thereby generate a spatially focused field in the tissue.

In some embodiments, each of the at least one sub-wavelength structure is coupled to a respective independent radio-frequency port.

An apparatus configured to transfer wireless power through tissue is also provided, comprising a plurality of sub-wavelength structures configured and arranged to generate propagating fields inside tissue and thereby generate a spatially adaptable electromagnetic field in the tissue, a plurality of independent feed ports configured and arranged to individually excite a respective one of the plurality of sub-wavelength structures thereby generating the spatially adaptable electromagnetic field, and a controller configured to redistribute a peak surface electromagnetic field to increase an allowable radio frequency output power.

In some embodiments, the plurality of sub-wavelength structures are further configured and arranged to generate an adaptive steering field in tissue.

In other embodiments, the spatially focusing and adaptive steering field/signal has a frequency between 300 MHz and 3000 MHz.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 2 shows the magnetic field that results from a conventional inductively coupled loop source.

FIG. 3C shows the magnetic field that results from an aperture coupled circular slot sub-wavelength structure.

FIG. 3E shows the magnetic field that results from a half slot sub-wavelength structure.

FIG. 4A shows an implanted device in a human patient being wirelessly powered by a mid-field propagating wave technique.

FIGS. 4B-4C show wireless power transmission with an inductively coupled approach (FIG. 4B) and a mid-field propagating wave approach (FIG. 4C).

FIG. 8 shows several arrangements of sub-wavelength structures and representative tissue.

FIGS. 10A-10G show midfield power transfer realization with a patterned metal plate.

FIG. 16 shows a table with fabrication process and power consumption values.

DETAILED DESCRIPTION

Figure 1A:
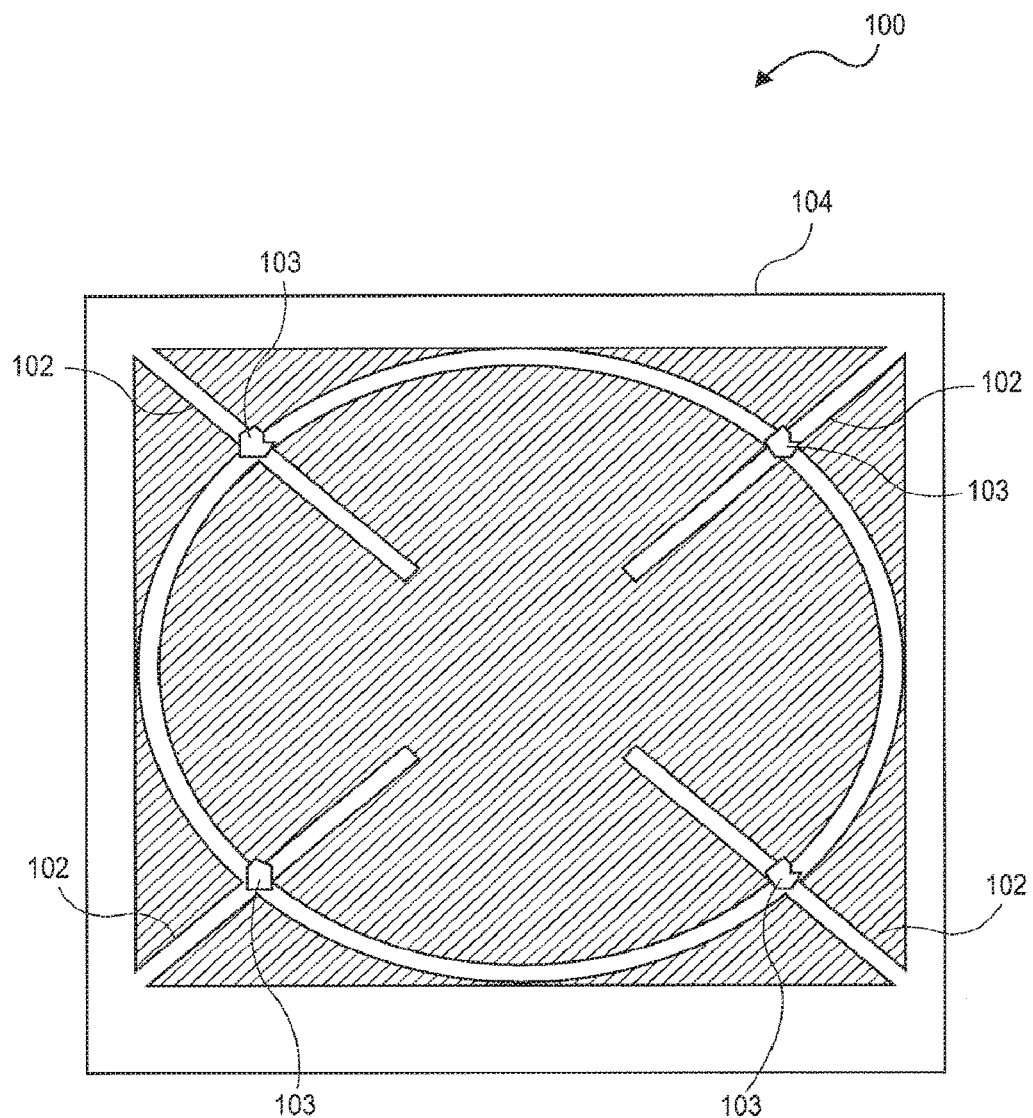
FIGS. 1A-1N show various embodiments of an external wireless power transmitting module.

Implantable devices and/or sensors can be wirelessly powered by controlling and propagating electromagnetic waves in a patient's tissue. The implantable devices can be implanted in humans or in other animals such as pets, livestock, or laboratory animals such as mice, rates, and other rodents. Such implantable devices/sensors can be implanted at target locations in a patient, as non-limiting examples, to stimulate areas such as the heart, and/or to sense biological, physiological, chemical attributes of the blood, tissue, and other patient aspects. Difficulties in achieving wireless power transfer can occur in the mismatch between the size of the implantable devices/sensors and the power transfer source, the depth of the devices/sensors in a patient, and additionally the spatial arrangement of the devices/sensors relative to the power transfer source.

Various aspects of the present disclosure are directed toward apparatuses or methods as exemplified or supported by aspects of the above noted description/embodiments, as well as the description/embodiments of the attached appendices. For instance, certain embodiments of the present disclosure are directed to manipulation of evanescent fields outside a patient's tissue to excite/control propagating fields inside the patient's tissue and thereby generate a spatially focusing and adaptive steering field/signal in the tissue.

Each of the sub-wavelength structures described above can be connected to a respective port in order to manipulate evanescent fields to excite/control propagating fields inside a patient's tissue. These propagating fields can be further manipulated to generate a spatially focusing and adaptive steering field/signal in the tissue. Any sub-wavelength structure that yields transverse magnetic fields dominating near the source, will minimize the tissue heating effect. These sub-wavelength structures can be configured to generate a magnetic near field that is in parallel with the tissue interface, and that is perpendicular with the propagating wave that transmits wireless energy. In certain embodiments, as shown above, an arrangement can include one, two, three, or four or more sub-wavelength structures are used to manipulate the evanescent fields. In other embodiments, two or more of the arrangements shown above can be combined such that even more sub-wavelength structures (e.g., six, eight, twelve) are used to manipulate the evanescent fields.

In certain embodiments, an arrangement can include two, three, four, or more sub-wavelength structures that can be configured to manipulate the evanescent fields. In other embodiments, two or more of the arrangements shown above can be combined such that even more sub-wavelength structures (e.g., six, eight, twelve, or more) are used to manipulate the evanescent fields.

Various aspects of the present disclosure include apparatus and methods directed to multiple sub-wavelength structures configured to generate a spatially adaptable electromagnetic field/signal (e.g., a midfield electromagnetic field) in a patient's tissue. The sub-wavelength structures can each be connected to an independent feed port that individually excites a respective one of the sub-wavelength structures, thereby generating the spatially adaptable electromagnetic field/signal. The independent feed ports and the sub-wavelength structures (such as patterned coils, conductors, and the like) are adapted to redistribute the peak surface electromagnetic fields in order to increase the allowable radio frequency output power in accordance with regulations from the apparatus.

In certain embodiments, the sub-wavelength structures manipulate evanescent fields to excite/control propagating fields and thereby generate a spatially focusing and adaptive steering field/signal in tissue.

Various aspects of the present disclosure include apparatus and methods directed to multiple sub-wavelength structures that generate and receive a spatially adaptable electromagnetic field/signal, which may include a power signal and a communication data signal. Additionally, aspects of the present disclosure may also include multiple sub-wavelength structures that generate a spatially adaptable electromagnetic field/signal and to provide and receive a spatially adaptable electromagnetic signal in multiple frequency bands.

Certain aspects of the present disclosure are also directed toward implantable devices that receive power transmitted via the sub-wavelength structures that transmit a spatially adaptable electromagnetic field. The implantable device, consistent with various aspects of the present disclosure, can be a size such that the device is deliverable via a catheter, cannula, or a needle. Additionally, the implantable device(s) can include a coil that receives the energy from the spatially adaptable electromagnetic field. In such an embodiment, the spatially adaptable electromagnetic field/signal is received as magnetization due to current in the coil. Further, the implantable devices can also include, in certain instances, a multi-turn coil that receives the spatially adaptable electromagnetic signal, rectifying circuitry that converts the spatially adaptable electromagnetic signal using AC-DC power conversion, and control circuitry to regulate pulse amplitudes, duration, and frequency.

Additionally, in certain embodiments, the sub-wavelength structures, consistent with various aspects of the present disclosure, adjust an operating frequency of the spatially adaptable electromagnetic signal to adjust the power of the implantable device or sensor. In some embodiments, the spatially adaptable electromagnetic signal can have frequency between 300 MHz and 3000 MHz.

Various aspects of the present disclosure are directed toward powering of one or more active implantable sensors or devices using a single power source. The types of implantable devices/sensors that can be powered using the single power source, consistent with various aspects of the present disclosure, are numerous. For instance, the implantable devices can be used for muscular stimulation, stimulation/sensing to regulate a patient's heart beat, multisite deep brain stimulation, drug delivery, and/or biological, physiological, and chemical sensing.

The devices disclosed herein can be individually addressable and independently controlled. Thus, the devices, for example as those used for muscular stimulation, can be placed at different locations corresponding to different muscle groups, and perform stimulation in a synchronized manner. Similarly, brain stimulation devices can be placed at different locations in the brain, and stimulation can be performed in a synchronized manner. The same can be said with drug delivery devices. Moreover, because the devices can be individually addressable and independently controlled, the devices can be activated and/or powered asynchronously as well as synchronously. These devices, in certain instances, can have characteristics dimensions in that the devices are much smaller (e.g., one, two, or three orders of magnitude) than their depth in tissue. Similarly, the devices, in certain instances, can have characteristics dimensions in that the devices are much smaller (e.g., one, two, or three orders of magnitude) than the source that provides the power to the devices.

The aspects of the present disclosure, as directed toward apparatuses, devices, and methods, can be utilized alone or in combination with various other aspects.

The structures described herein can be used with sensors/devices that include feedback to the sub-wavelength structures. These types of sensors can include, for example, implantable temperature sensors or imaging devices. In this manner, the devices are responsive to the structures illustrated above that generate a spatially adaptable electromagnetic field/signal. The feedback-type devices respond to the power and/or data portions of the signal provided by the spatially adaptable electromagnetic field/signal, and are prompted to respond. For instance, temperature sensors located in a patient will broadcast/report the temperature of the tissue in response to the power and/or data portions of the signal provided by the spatially adaptable electromagnetic field/signal. Additionally, imaging devices implanted in a tissue can broadcast/report the captured images in response to the power and/or data portions of the signal provided by the spatially adaptable electromagnetic field/signal. Moreover, the penetration depth of the spatially adaptable electromagnetic field/signal can be modeled and controlled. Thus, in certain embodiments, the feedback devices can indicate and label data, in response to the spatially adaptable electromagnetic field/signal, to record the depth at which the device is operating. By storing this data on a patient-by-patient basis in a storage device, a computer can access and analyze this data for statistical purposes.

By storing the position or label of the feedback-type device in a memory circuit via a programmable computer, various patient feedback tracking methods can also be realized. For instance, the depth of an implantable imaging device can be optimized by analyzing the surrounding tissue. In this manner, the depth of the implantable imaging device can be adjusted if it is determined that a more optimal position is possible. Similarly, the depth of an implantable stimulation device can be used to determine the heath of the tissue area surrounding the stimulation device, and determine an optimal positioning of the device in response to the spatially adaptable electromagnetic field/signal. Additionally, the feedback-type devices can respond to the spatially adaptable electromagnetic field/signal and broadcast data stored in a memory circuit. Thus, the feedback-type devices can continuously update a physician of the data that is being tracked by the device. This allows for real-time monitoring, diagnosing, and/or treating a patient wirelessly.

Implantable devices/sensors can be wirelessly powered by controlling and propagating electromagnetic waves in tissue. The implantable devices can be implanted in humans or in other animals such as pets, livestock, or laboratory animals such as mice, rats, and other rodents. Such implantable devices/sensors can be implanted at target locations in a patient, as non-limiting examples, to stimulate areas such as the heart, and/or to sense biological, physiological, chemical attributes of the blood, tissue, and other patient aspects. Difficulties in achieving wireless power transfer can occur in the mismatch between the size of the implantable devices/sensors and the power transfer source, the depth of the devices/sensors in a patient, and additionally the spatial arrangement of the devices/sensors relative to the power transfer source.

Various aspects of the present disclosure are directed toward apparatuses or methods as exemplified or supported by aspects of the above noted description/embodiments, as well as the description/embodiments of the attached appendices. For instance, certain embodiments of the present disclosure are directed to manipulation of evanescent fields outside a patient's tissue with sub-wavelength structures to excite/control propagating fields inside the patient's tissue and thereby generate a spatially focusing and adaptive steering field/signal in the tissue. A sub-wavelength structure generates fields that are evanescent in nature near the source. In contrast, in conventional wireless approaches using inductive coupling, the evanescent components outside tissue (near the source) remain evanescent inside tissue which does not allow for effective depth penetration.

This disclosure provides embodiments of sub-wavelength structures and methods for controlling the excitation of those structures to excite the propagating modes inside tissue from the evanescent modes outside tissue. As a result, this approach is very effective in transporting energy to absorption-limited depth inside tissue. The designs disclosed herein include structures that use tissue as a dielectric waveguide to tunnel energy into the body. The energy can be received by an implanted module which will be discussed below, to allow for wireless power transfer to implanted devices at depths unattainable with conventional inductive coupling technology.

This disclosure provides a midfield wireless powering approach that integrates an external module configured to transmit wireless power, and one or more implanted modules configured to receive wireless power that combines an impulse generator and at least one stimulation electrode together into a small, leadless, implantable device. In some embodiments, the implanted module can be small enough to be delivered via a catheter or a hypodermic needle. For example, the implanted module can be as small as a few millimeters in diameter (2-3 mm) down to having diameters on the order of 100's of microns or less. This implanted module allows for the transfer of wireless power to nearly any location in the body at performance levels far exceeding requirements for both complex electronics and physiological stimulation. Because the implanted modules are small, they can be injected into the targeted nerve or muscle region directly without the need for leads and extensions, to provide sensing and stimulation to the targeted nerve, muscle, or tissue region.

Figure 1B:
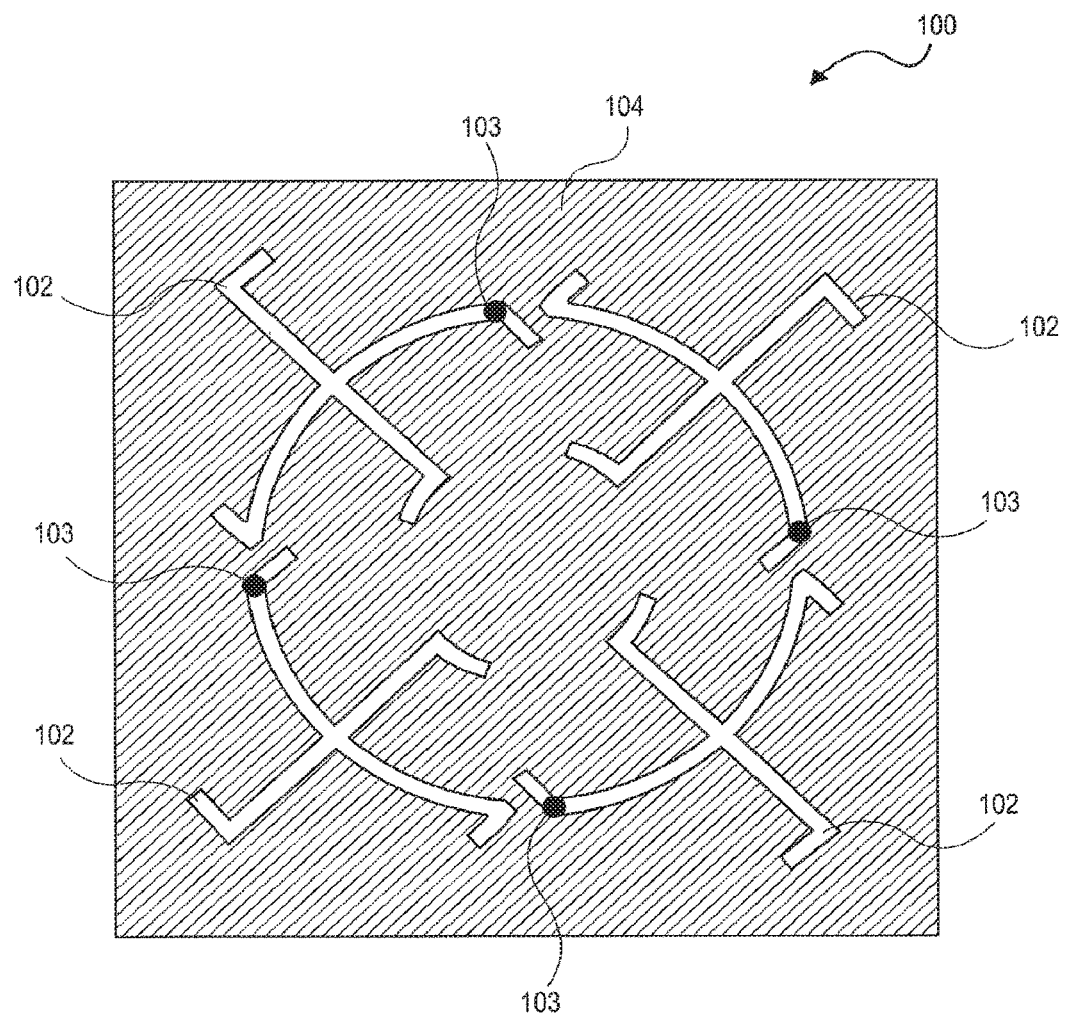
Figure 1I:
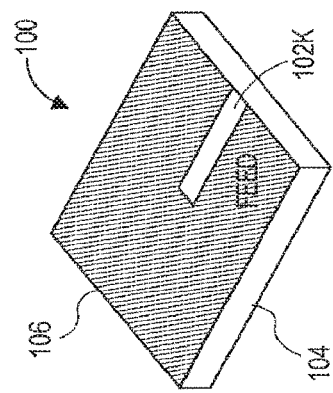
Figure 1J:
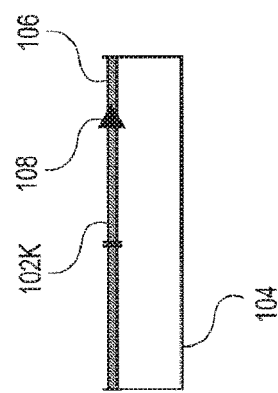
Figure 1K:
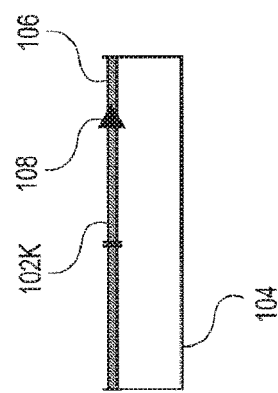
Figure 1L:
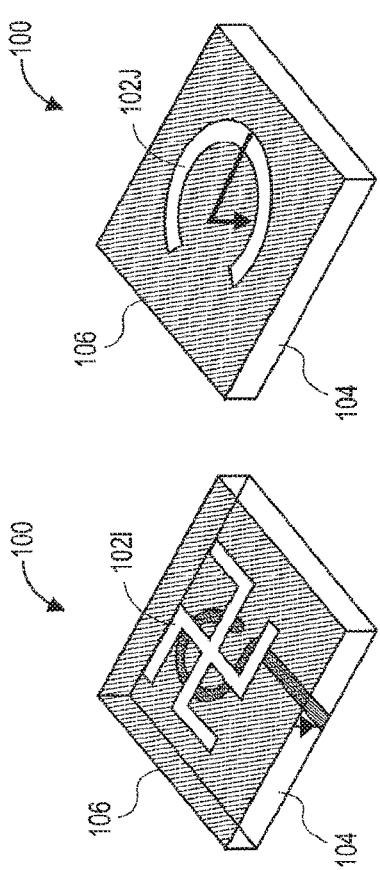
Figure 1M:
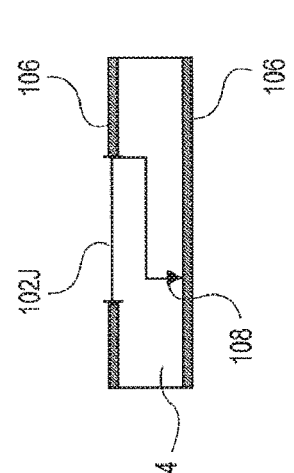
Figure 1N:
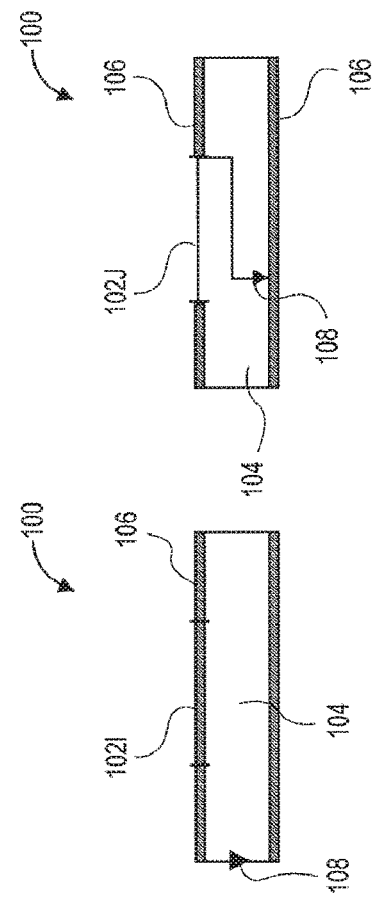

For illustrative purposes, FIGS. 1A-1N show various embodiments and views of wireless power transmitting modules 100, including one or more sub-wavelength structures 102, consistent with various aspects of the present disclosure. A sub-wavelength is defined with respect to the wavelength of the field outside a patient's tissue or in the air. A sub-wavelength structure can be of a dimension less than the wavelength in air but might be comparable to the wavelength in tissue. For example, at 1.6 GHz, the wavelength in muscle is about 7.3 times smaller than the wavelength in air. Any source structure that is of dimension on the order of the wavelength in muscle or tissue may be a sub-wavelength structure. FIGS. 1C-1E show perspective views of three specific embodiments of wireless power transmitting modules, and FIGS. 1F-1H show side views of those modules, respectively. Similarly, FIGS. 1I-1K show perspective views of some wireless power transmitting modules, and FIGS. 1L-1N show side views of those modules, respectively.

The sub-wavelength structures of FIGS. 1A-1N can be configured to manipulate evanescent fields outside a patient's tissue to excite/control propagating fields inside the patient's tissue to generate a spatially focusing and adaptive steering field/signal in the tissue. The wireless power transmitting modules 100 shown in FIGS. 1A-1N can include the sub-wavelength structure(s) 102 disposed over a substrate 104 and one or more ground plane(s) 106 (shown in the side views of FIGS. 1F-1H and 1L-1N. In some embodiments, the sub-wavelength structures 102 can comprise a conductive material, such as a copper. The substrate can comprise an insulating material, such as an epoxy, or a ceramic. The substrate can be a solid, rigid, substrate, or alternatively can be a flexible substrate configured to conform to the skin surface of patients. In some embodiments, the sub-wavelength structures 100 can further comprise a ground plane bonded to or disposed on the substrate. The ground plane can be disposed on a top surface (FIGS. 1H, 1L, 1N), a bottom surface (FIG. 1F, 1G), or both top and bottom surfaces (FIG. 1M) of the substrate.

The design of each sub-wavelength structure can be varied depending on the design requirements of the specific application. FIGS. 1A-1B both show a wireless power transmitting module having a plurality of sub-wavelength structures 102, wherein the sub-wavelength structures resemble X' with curved or protruding strips or features. In both these embodiments, each of the sub-wavelength structures 102 can be excited by one or more independent radio-frequency ports 103 connected to a voltage and/or current source. In some embodiments, the sub-wavelength structures can be excited with a voltage ranging from 0.1 V to 10's V, or can be excited with a current ranging from 0.1 A to 10's A. The frequency range of the source can range from 300 MHz to 3 GHz. For appropriate phases between the port signals, the sub-wavelength structures can generate circular current paths that mimic the optimal current density. When positioned above tissue, the structures couple power from the external circuitry into the tissue volume with high efficiency (>90%), as evidenced by both low levels of backside radiation and a pronounced minimum in the scattering parameter spectrum.

Degrees of freedom provided by the phases of the input port signals enable various interference patters to be synthesized, including those with spatially shifted focal regions. Software control of these phases can refocus the fields without mechanical reconfiguration, which can be useful for implanted devices inserted on rhythmic organs or for locomotive devices. In some embodiments, a "greedy" phase search algorithm can be implemented based on closed-loop feedback that obtains focusing-enhanced power transfer in real-time. In other embodiments, the feedback signal can be wirelessly transmitted from the implanted device to the midfield source.

FIGS. 1C and 1F show a patch sub-wavelength structure 102c, disposed over a substrate 104 with a ground plane 106 on a bottom surface of the substrate. A feed 108 is also shown in FIG. 1F, which is used to feed or transmit electrical signals to or from the sub-wavelength structure. FIGS. 1D and 1G illustrate a PIFA sub-wavelength structure 102d, disposed over a substrate 104 with a ground plane 106 on a bottom surface of the substrate. The feed 108 is shown in FIG. 1O, along with a short 110 connected to the structure 102d. FIGS. 1E and 1H show a slot sub-wavelength structure 102e in a ground plane 106 disposed over a substrate 104. The feed 108 is shown in FIG. 1H. FIGS. 1I and 1L show a cross slot sub-wavelength structure 102i in a ground plane 106 disposed over a substrate 104. The feed 108 is shown in FIG. 1L. FIGS. 1J and 1M illustrate an aperture coupled circular slot sub-wavelength structure 102j in a ground plane 106 disposed over a substrate 104. This embodiment can further include a ground plane 106 on a bottom surface of the substrate. The feed 108 is shown in FIG. 1M. Finally, FIGS. 1K and 1N illustrate a half slot sub-wavelength structure 102k, disposed over a substrate 104 with a ground plane 106 on a top surface of the substrate. The feed 108 is shown in FIG. 1N. In all the embodiments described above and illustrated, one or more power source(s) and amplifier(s) can be connected to the sub-wavelength structure(s) via the feeds (or ports) to manipulate evanescent fields. Furthermore, in some embodiments, each sub-wavelength structure can include one or more feeds or ports.

The wireless power transmitting modules 100 described above generally include one or more sub-wavelength structures, one or more excitation ports, a substrate, and one or more ground planes. The modules 100 can be controlled by a controller (both hardware and software) to dynamically shift a focal region of the electromagnetic field.

Some discussion on various techniques for transferring wireless power will now be described. FIG. 2 shows the magnetic field 212 generated by a conventional inductively coupled loop source 214, in both the yz and xz planes. As can be seen, the magnetic field is generated perpendicular to the tissue interface 216, and is parallel with the direction of desired wireless power transfer to an implant disposed in tissue below the loop source, such as an implanted device 218.

FIG. 8 shows several arrangements of sub-wavelength structures and representative tissue, consistent with various aspects of the present disclosure.

Figure 3A:
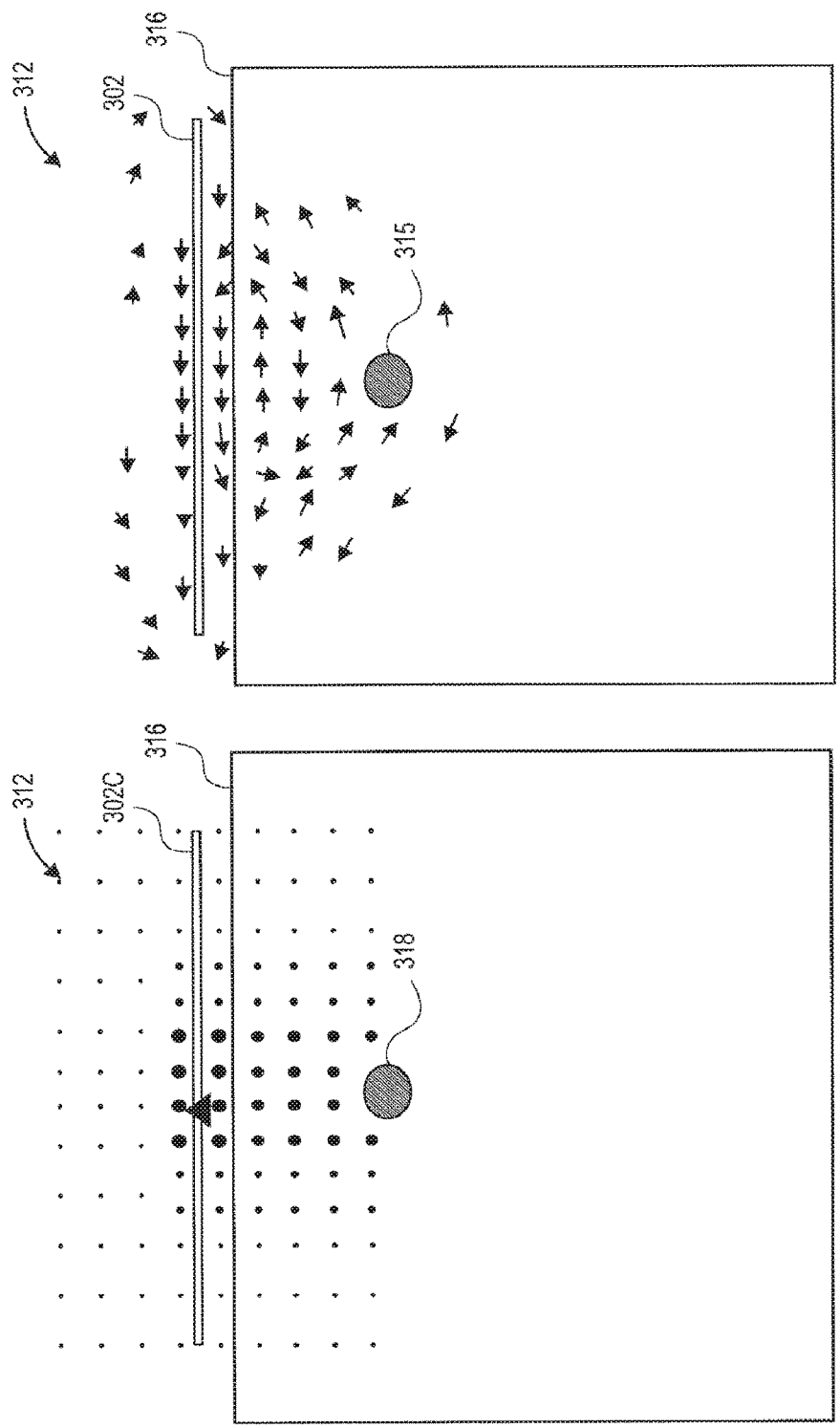
FIG. 3A shows the magnetic field that results from a patch sub-wavelength structure.
Figure 3B:
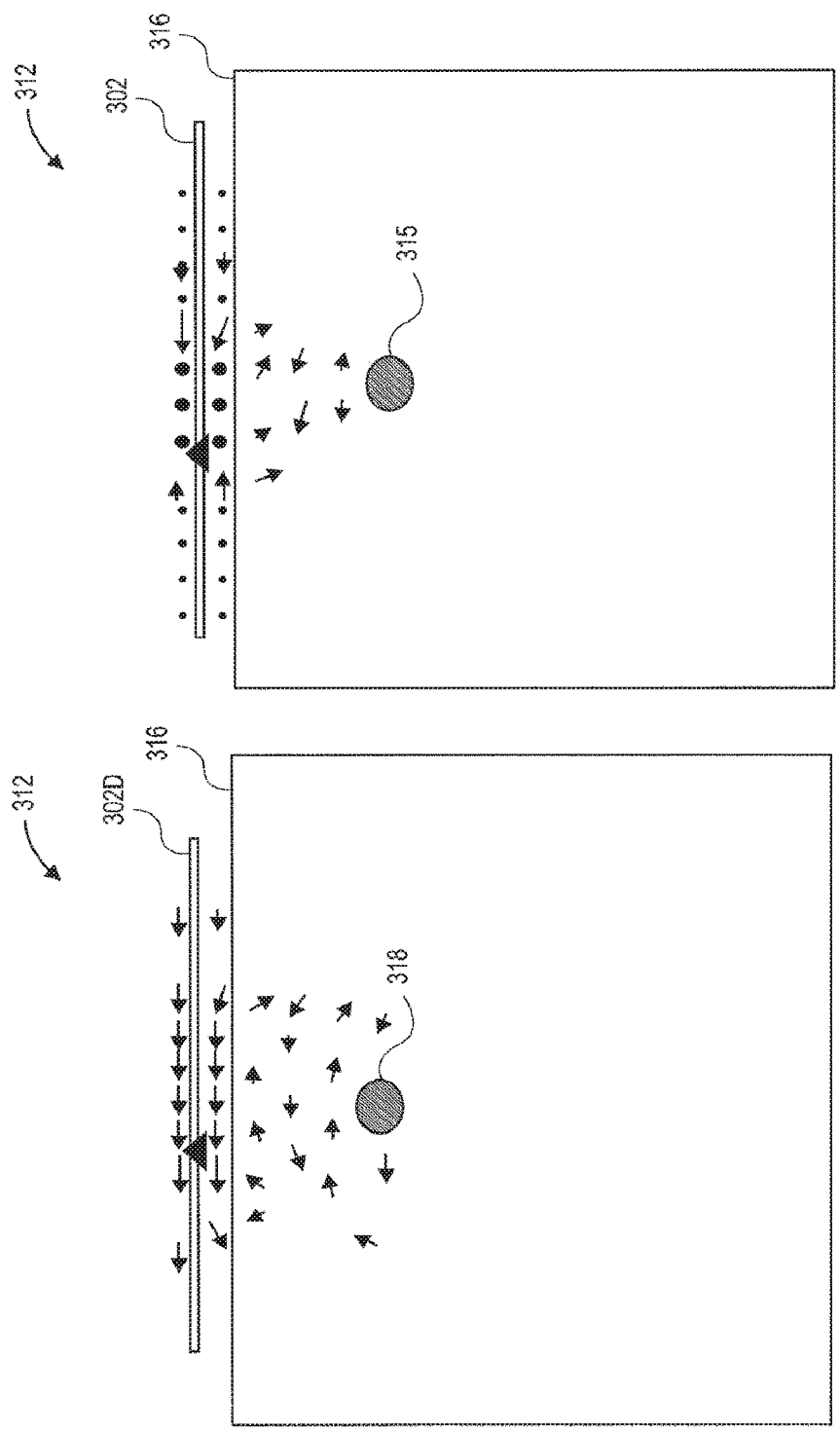
FIG. 3B shows the magnetic field that results from a PIFA sub-wavelength structure.
Figure 3D:
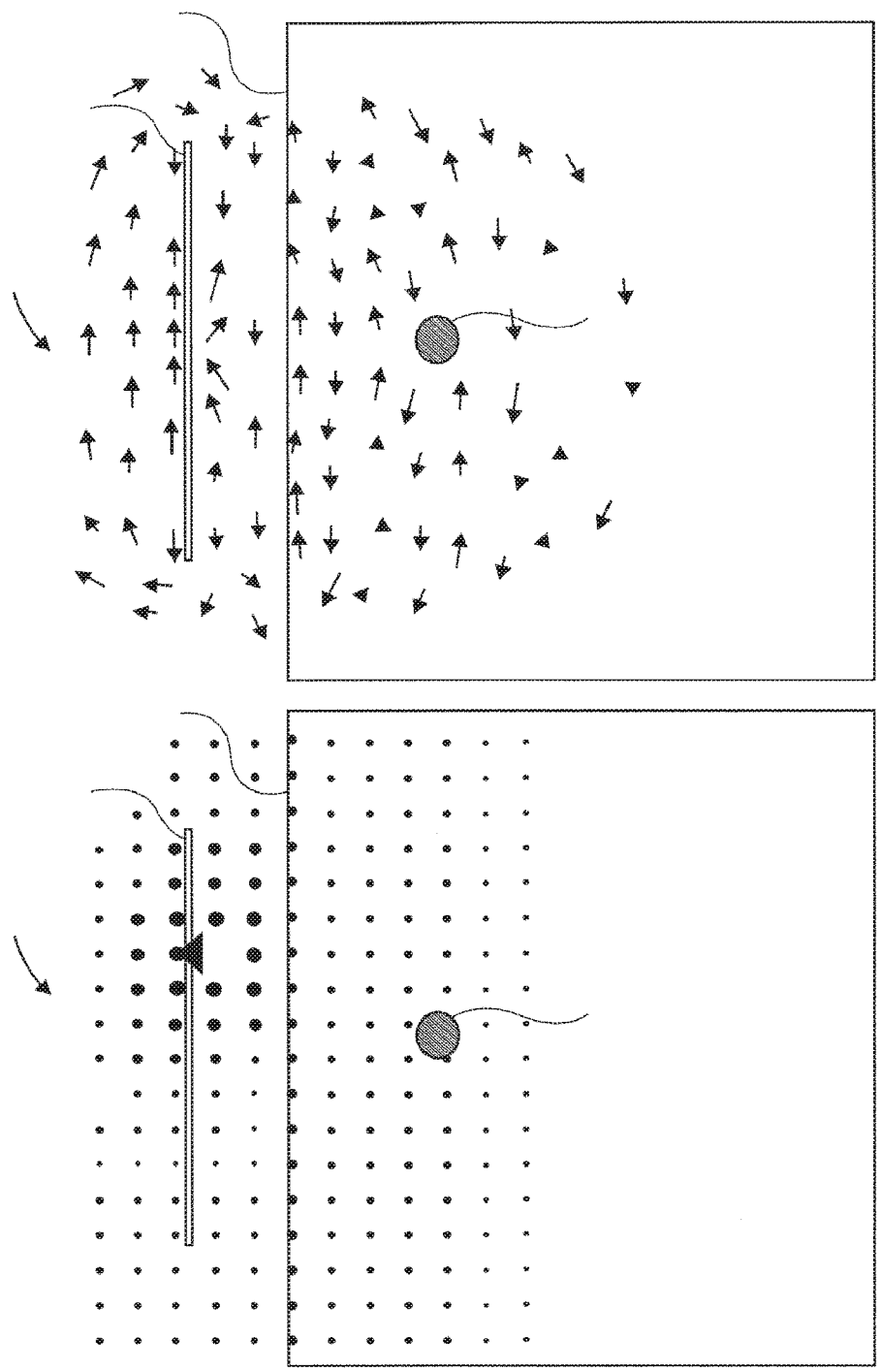
FIG. 3D shows the magnetic field that results from a cross slot sub-wavelength structure.

In contrast, FIGS. 3A-3E show the magnetic fields 312 produced by various sub-wavelength structures of the present disclosure. These structures generate a magnetic field 312 parallel to the tissue interface 316, and perpendicular to a propagating wave generated in tissue that transmits wireless power to an implanted device 318. FIG. 3A shows the magnetic field generated with a patch sub-wavelength structure 302c (FIGS. 1C and 1F) in the yz and xz planes. FIG. 3B shows the magnetic field generated with a PIFA sub-wavelength structure 302d (FIGS. 1D and 1O) in the yz and xz planes. FIG. 3C shows the magnetic field generated with a cross slot sub-wavelength structure 302i (FIGS. 1I and 1L) in the yz and xz planes. FIG. 3D shows the magnetic field generated with an aperture coupled circular slot structure 302j (FIGS. 1J and 1M) in the yz and xz planes. FIG. 3E shows the magnetic field generated with a half slot sub-wavelength structure 302k (FIGS. 1K and 1N) in the yz and xz planes.

FIG. 4A shows a wireless power transmitting system including a wireless power transmitting module 400 and an implanted device 418 inside a human body. In FIG. 4A, the device is shown implanted in a chest cavity of the patient, such as in or near the heart. It should be understood from this figure that the implanted device can be placed anywhere in the body, such as in the heart, brain, lungs, spinal cord, bones, nerves, sinuses, nasal cavity, mouth, ears, peritoneal cavity, arms, legs, stomach, intestines, digestive tract, kidneys, bladder, urinary tract, or any other organ or part of the body that can benefit from the sensing and/or stimulation features provided by the systems described herein.

In FIG. 4A, the transmitting module 400 can be positioned above the skin of the patient, and the implanted module comprising a receive coil can be implanted in the patient. Power transfer occurs when the interaction of the source fields with the coil structure results in work extruded by a load in the implanted module. For a sub-wavelength coil, only the lowest order mode is important and the transfer mechanism can be described by electromagnetic induction characteristics of dynamic magnetic field interactions. The electric and magnetic fields generated by a time-harmonic current density Js on the surface of the source conductor can be solved by decomposing the current density into its spatial frequency components. Each component corresponds to a plane wave with propagation determined by phase matching conditions for refraction and reflection over planar boundaries, from which the total field in tissue can be recovered at each depth z by integration over the source spectrum.

The properties of the mid-field region are key to optimal powering. The sub-wavelength structures manipulate evanescent fields to excite/control propagating waves (alternating electric and magnetic fields) and thereby generate a spatially focusing and adaptive steering field/signal in tissue that converges on the implanted device. Back-propagation of fields at the focal plane to the surface of the skin reveals that the source is highly oscillatory and composed of significant evanescent components that are important only in the near-field. In contrast with conventional near-field powering, however, these evanescent components excite propagating modes in tissue that transport energy to absorption-limited depths.

FIGS. 4B-4C show the difference between the ability of a near-field or inductively coupled wireless power transfer system (FIG. 4B) to transfer power into a depth of tissue compared to the mid-field design (FIG. 4C). of the present disclosure. As seen in FIG. 4C, the mid-field design of the present disclosure allows for transmission of wireless power to a depth in tissue not attainable by inductively coupled systems.

In some embodiments, a focal point of the wireless power transfer system of the present disclosure can be adjusted to change a direction of the propagating wave. FIG. 4C illustrates formation of a propagating wave in a direction directly below the external module, along line 419a. However, in some embodiments, the focal point can be adjusted to cause the propagating wave to travel in a steer direction through the tissue, such as along lines 419b or 419c. This adjustment can be attained by adjusting a phase and/or amplitude of one or more of the sub-wavelength structures of the external module.

Figure 5B:
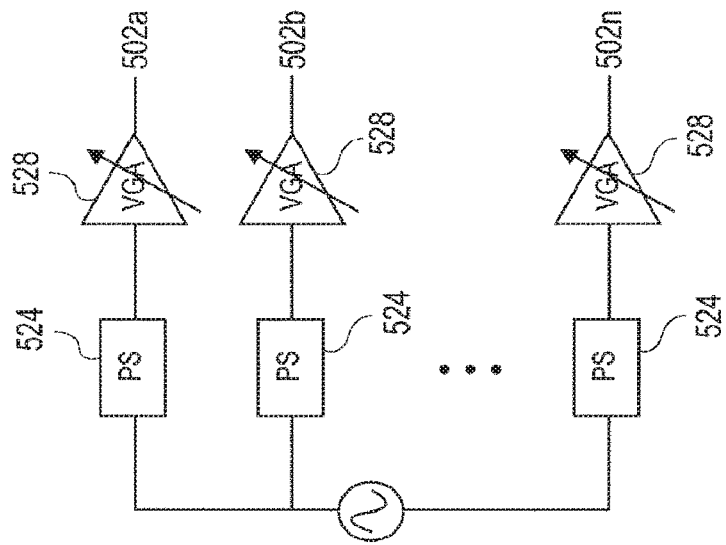
FIGS. 5A-5B are schematic diagrams of architectures for a controller of the external module of FIGS. 1A-1N.
Figure 5A:
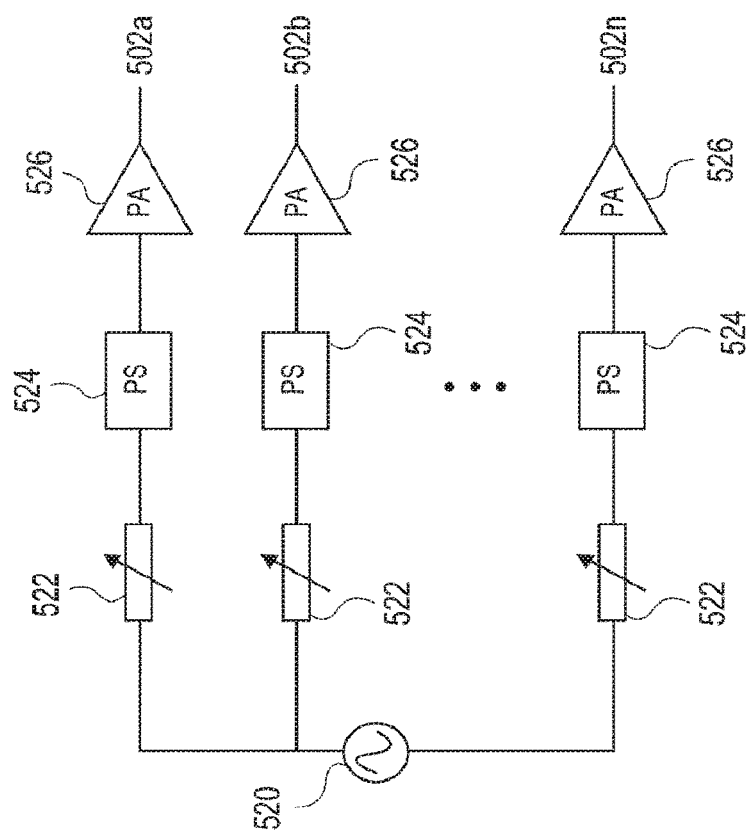

FIGS. 5A-5B shows two embodiments of architectures for a controller of the wireless power transmitting modules described herein, for exciting the ports of the sub-wavelength structures. These architectures can be configured to control one or more sub-wavelength structures 502a-502n of the wireless power transmitting modules. In each architecture, the RF signal can be sourced from an oscillator 520, and be divided symmetrically into multiple RF signals through a power divider. In the architecture of FIG. 5A, the signal is then fed through attenuator(s) 522 with variable controllable attenuation settings. The signals can then be fed through phase shifter(s) 524 with controllable phase, and then amplified with amplifier(s) 526. This architecture produces controlled phase and amplitude signals at each port of the module. The architecture on in FIG. 5B is configured to produce the same controlled phase and amplitude signals, but with fewer components by combining the amplifier(s) and the amplitude control element(s) into a single component 528.

Implanted Module.

Figure 6:
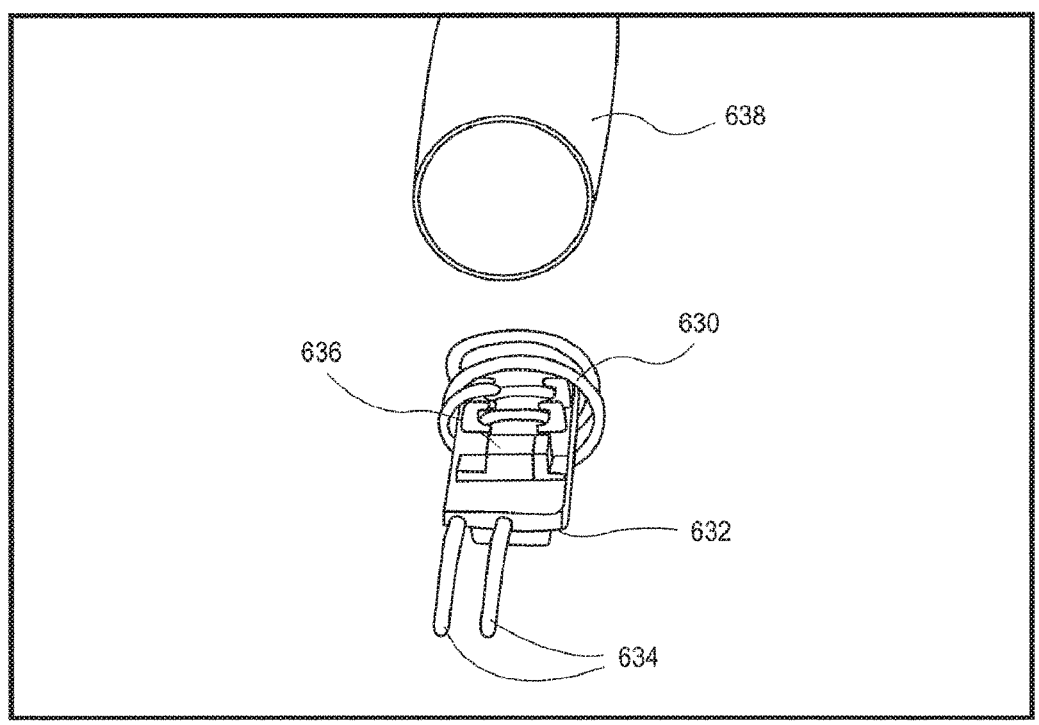
FIG. 6 shows one embodiment of an implanted device configured to receive wireless power from the external module of FIGS. 1A-1N.

One embodiment of an implanted module for receiving wireless power is shown in FIG. 6. The implanted module can include a coil 630 disposed over an integrated chipset (IC) 632. The coil 630 can be a loop (or multiple loops) of a conductor. In some embodiments, the coil 630 has a diameter of less than 2 mm. The coil can be configured to receive the wireless power transmitted from the external modules described herein. The module can optionally include features 634 for sensing and/or stimulating tissue, such as electrode(s) or sensors. The electrodes can comprise, for example, screw-type electrodes, planar electrodes, or cuff electrodes. In other embodiments, the sensors can comprise biopotential sensors, pressure sensors, 02 sensors, etc. The implanted module can optionally include electrical components for the storage of energy, such as a capacitor or battery 636. Due to the small size of the implanted module (2 mm or less in diameter), the implanted module can be delivered and implanted into a patient with minimally invasive techniques, such as with a catheter 638, a cannula, a needle, or the like.

Because the power levels supported by a midfield wireless powering approach far exceed requirements for microelectronic technologies (e.g., in one embodiment, an input power level of 500 mW from the external module can deliver approximately 200 uW of power over 5 cm of tissue to a 2 mm diameter implant coil), more sophisticated functions can be implemented such as real-time monitoring of chronic disease states or closed-loop biological sensing and control by the implanted module. Hence, in some embodiments, the implanted module can include one or more of the following building blocks:

Power Management.

Figure 7A:
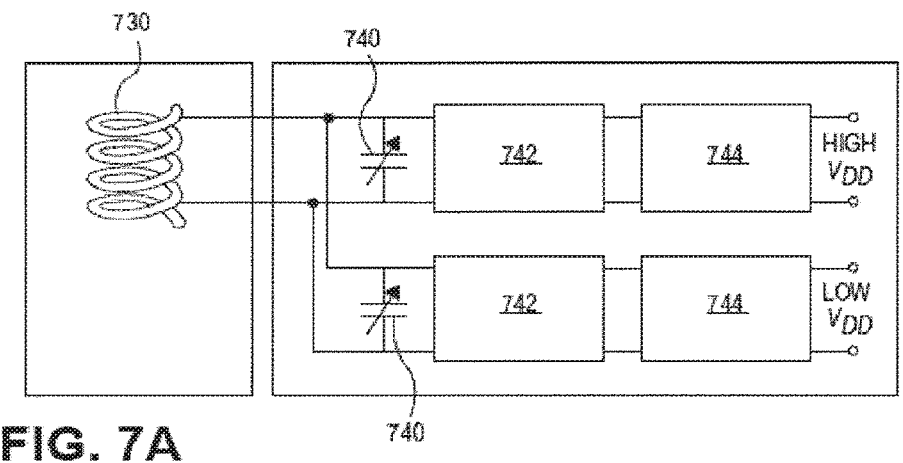
FIGS. 7A-7C show embodiments of architectures for a controller of the implanted device of FIG. 6.

To increase the efficiency of rectification and power management of wirelessly powered implants operating in the electromagnetically weakly coupled regime, AC-DC conversion circuits in the implanted module can be divided into the low-voltage and high-voltage domains. FIG. 7A shows an architecture that can be included in the IC of the implanted module to handle the power management features of the implant. FIG. 7A shows a coil 730 electrically connected to one or more capacitors (or variable capacitors) 740, multistage rectifiers 742, and regulators 744, to divide the AC-DC conversion circuits into low-voltage and high-voltage domains.

Battery Storage.

A rechargeable battery such as thin film battery can be included in the implanted module for temporary energy storage and for use as an efficient charge pump for the power management circuitry. In some embodiments, the thin film battery can be stacked to increase the energy density.

Power Detection.

The instantaneous power level received by the implanted module can be detected and sent via a data transmitter to the external module for adaptive focusing onto the implant module in the midfield. Data can be transmitted between the implanted module and the external module through a wireless link. In some embodiments, the wireless link can operate in the frequency range of the power transmission, or in other embodiments, the wireless link can operate in a different frequency range. The detected power level can be used in a closed-loop feedback control with the controller of the system to adjust and focus the external module for optimal wireless power transfer.

Pulsed RF Modulation.

Conventional load modulation does not work in the midfield due to the low quality factor of the implant antenna, leading to poor signal-to-noise ratio and substantial link margin fluctuation. To overcome this problem, the data transmitter of the implanted module can use pulsed RF modulation. To ease detection at the external module, the data and power carriers can operate at different center frequencies.

Programmable Current Drivers.

Stimulation applications differ mainly by the characteristics of the electrical pulses such as intensity, duration, frequency, and shape. The current drivers for stimulation are designed to support wide range of these parameters and can be programmed via the wireless data link. The current drivers can also be configured to support actuation such as locomotion.

Programmable Digital Core.

The digital core coordinates the interaction among various blocks in the implanted module, communication between the implant and external modules, and the multi-access protocols. Each implant module can have its own identification (ID) such as via an ID stored in the memory of the implanted module.

Data Receiver and Transmitter.

Figure 7B:
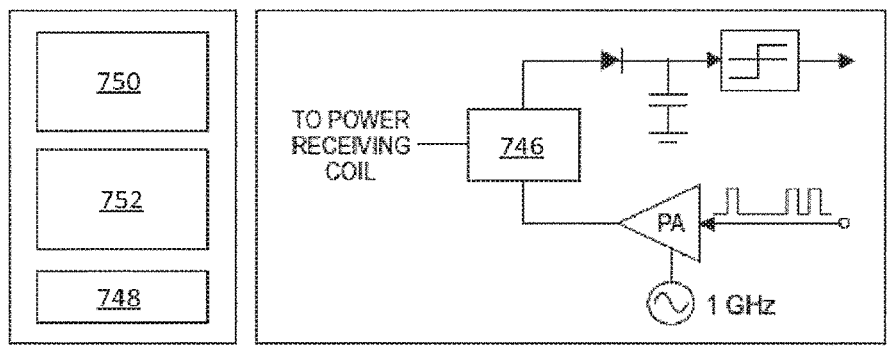

The external module can remotely communicate with each implanted module to program or configure each implanted module via the data receiver. FIG. 7B shows one embodiment of a data receiver based on envelop detection and a data transmitter based on an ultra-wideband architecture. The receiver and transmitter can be time multiplexed by a T/R switch 746 connecting to the power receiving coil or to a separate antenna. Each implanted module can have its own ID 748 for multi-access. A digital controller 750 can be implemented to handle the multi-access protocol 752, commands from the external module, and feedback data to the external module.

Sensing Frontend.

Figure 7C:
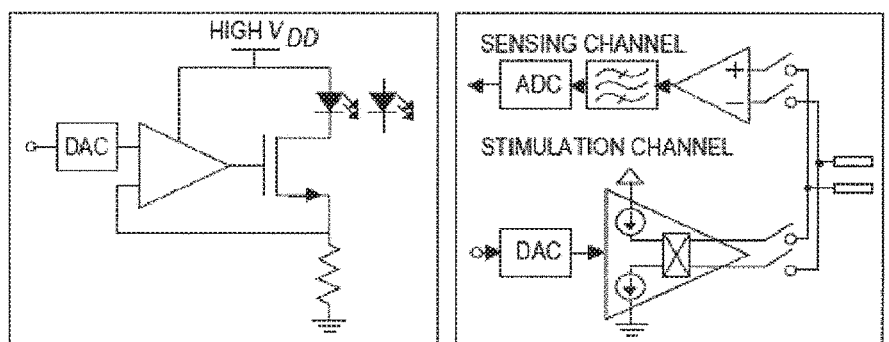

The sensing frontend can comprise pre-amplifiers, analog-to-digital converters (ADC) to discretize signals from the pre-amplifiers, and drivers for the sensors. Signals from the output of the ADCs can either be stored in the non-volatile memory of the implanted module or sent to the external module via the Pulsed RF modulator. In addition, the sensed signals can provide biological feedback for adjusting parameters of the current drivers. FIG. 7C shows the architecture for one or multiple LED drivers, and the electrical sensing and stimulation frontends. The LED drivers can be connected to LEDs for optical stimulation of tissue (nerves). The electrical sensing and stimulation frontends can also be connected to electrodes for sensing the biological activities and altering the electrical pathways.

Non-Volatile Memory.

Flash memory, for example, can be included to record usage model of the implant module such as the time of activation and setting of the current deriver, and/or to store measurements from the sensing frontend.

Modular Construction.

The implanted module can be customizable depending on the particular needs or requirements of the end user. For example, the implanted module can include a number of base components including the wireless power receiving coil and the IC, and can further include an interface that can receive any type of sensor or stimulator desired by the user. For example, the implanted module can be configured to receive any type of sensor, such as thermal, chemical, pressure, oxygen, PH, flow, electrical, strain, magnetic, light, or image sensors, or any type of stimulator, such as electrical, optical, chemical, or mechanical stimulators, or a drug delivery apparatus. The modular approach of the implanted module can therefore be customized to accommodate the particular needs of the user.

All the above building blocks in the implanted module can be integrated into a single die as system-on-chip (SoC) or multiple dies enclosed in a single module as system-in-package (SiP).

External Module.

The external module (described above) can be configured to energize and control the implanted modules, and to perform noninvasive readout through a bidirectional wireless link setup with the implanted modules. The external module can include one or more of the following building blocks:

Midfield Coupler.

FIGS. 1A-1N show various shapes and patterns for the external module or midfield coupler, which can include one or more sub-wavelength structures. The coupler can be made on solid substrate, or on a flexible substrate configured to conform to the skin surface of patients.

Dynamic Midfield Focusing Circuits and Algorithms.

Based on the power measurement feedback from the implant module, the external module can run an algorithm, for example, the greedy search algorithm, to change the phase and/or magnitude settings in each element of the midfield coupler so as to dynamically shift the focal region to the individual implant module. For example, the implanted module can detect a power level of received wireless energy, and the external module can automatically adjust the phase and/or amplitude of the sub-wavelength structures to adjust the focal point of the transmitted energy signal. This adjustment can be made automatically and in real time to optimize wireless power transmission between the external module to the internal module.

Bidirectional Wireless Link to the Implant Module.

The wireless link can activate the implanted module, program the setting of the implanted module, and download measurements from the sensing frontend of the implanted module. The data rate for the downlink; from the external module to the implanted module, can be a few Mbps or lower, while the data rate for the uplink; from the implant module to the external module should be higher, can be in the range of 1 Mbps or even higher.

Multiaccess Protocols.

These protocols can coordinate the implanted modules to carry out synchronous tasks such as coordinated multi-site stimulation. In some embodiments, multi-access schemes can be time multiplexing and frequency multiplexing.

Patient/Clinician User Interface.

A peripheral device including a display can be integrated with the external module to interface with a patient and/or clinician. In other embodiments, the integrated peripheral device can be replaced by a bidirectional wireless link communicating with a smartphone or a tablet. In this embodiment, the patient and clinician can interface with the external module using the display of the smartphone or tablet through the wireless link.

In some embodiments, the entire external module can be integrated into a palm-size device and held by the patient for on-demand applications. It can also be worn on the body or affixed to the skin surface. Patients can use the external module to charge the battery of the implant modules as needed. In some embodiments, the implanted module(s) can be charged with only a few minutes of wireless charging per week/month. During charging, patients can also download usage record from the implant modules and send the record to the clinician for analyses.

Various aspects of the present disclosure are directed toward powering of multiple active implantable sensors or devices using a single power source. The types of implantable devices/sensors that can be powered using the single power source, consistent with various aspects of the present disclosure, are numerous. For instance, the implantable devices can be used for muscular stimulation, stimulation/sensing to regulate a patient's heart beat, multisite deep brain stimulation, drug delivery, and/or biological, physiological, and chemical sensing. The systems described herein can also be configured to be used in the following applications:

Cardio Pacemaker.

The implanted module can be delivered via a catheter through the vasculature into the right ventricle of a patient. A separate implanted module can be delivered through the coronary sinus into the coronary vein, and placed on the left ventricular epicardium. These implanted modules can include stimulation and sensing electrodes to apply leadless pacing to the heart. Thus, leadless biventricular pacing can be achieved with the present system with only minimally invasive procedures. In addition, the procedure time can be shortened substantially over prior approaches. This can also eliminate any complication during to the multiple leads and extensions.

Deep-brain stimulation. Current procedure involves the drilling of holes with diameter >1 cm in the skull to insert a lead and the extension from the lead to the stimulating module. Due to the invasiveness of the procedure, only a limited number of target sites are selected for placing the electrodes. By contrast, the implanted modules in this disclosure, being very small, can be injected into the brain via other less invasive routes. Since there is no lead and extension wire in the present system, more target sites for stimulation can be supported. This results in less infection and lower regulatory risk.

Spinal cord stimulation. Batteries in newer models of spinal cord stimulator are rechargeable due to the high power requirement. However, their powering approaches are exclusively based on inductive coupling (or near-field coupling). Since the harvesting components are large in these systems, they can only be placed subcutaneously. Therefore, the lead and extension wires in these systems potentially restrict the location of the electrodes for effective stimulation. In this disclosure, the power-harvesting component in the implanted module is relatively tiny. The entire implanted module can be easily placed next to the targeted nerve region in the spinal cord and requires no lead wire connecting them. This results in less infection, less damage to the spinal cord tissue, and more effective stimulation.

Peripheral nerve stimulation. Most current devices support low-frequency stimulation and only a few of them support high-frequency low-intensity stimulation due to the much higher power requirement. The systems of this disclosure can support both modes. In addition, the bidirectional wireless link provides instant programmability, switching between different modes.

Stimulation to treat obstructive sleep apnea (OSA). The implanted modules of this disclosure can be injected and directly embedded into the muscular tissue near the tongue, and can deliver electrical stimulation to open the airway of a patient during sleep. Multiple implant modules can be injected into different muscular groups to intensify the muscle contraction. When needed, patients can charge the implanted modules with the external module and simultaneously, download a time stamp of each OSA episode. This information can be sent to the clinicians. Data collected can also be used to reprogram the implanted modules.

Medical sensors. Batteryless implanted sensors are typically passive in nature, that is, there is no active circuitry in the device to condition the sensed signals. To compensate for the poor signal quality, an external reader is needed to be very sophisticated and is usually large (cannot be fitted on a palm). In addition, not many stimuli can be detected by passive sensors. The lack of active implanted sensors is mainly due to the lack of an efficient wireless powering approach. For example, the inductive coupling approach used in the rechargeable impulse generator for spinal cord stimulation has limited penetration and the receiver (the implanted device) is large. The system of the present disclosure allows for the transfer of substantial amount of power to small implanted modules at nearly any location in the body from a palm-size external module. This enables an array of new sensing applications for continuous monitoring in the medical field, for example, post-surgery oxygen sensing in the heart and the brain.

Wireless endoscopes. Current capsule endoscope has limited battery lifetime, leading to incomplete small-bowel examination which is one of the major clinical failures. The implant module in our invention is small and has indefinite power supply, solving the deficiency of current endoscopes. In addition, since our implant module is many times smaller than the current capsule endoscope, patients can swallow multiple of the implant modules simultaneously. They are expected to orient differently in the intestine and therefore, can take pictures from different angles at the same location, improving the field of view. The images collected from them will improve the diagnosis. Finally, the probability of retention is expected to be dramatically reduced, avoiding the need of surgical or endoscopic retrieval.

Implanted drug delivery. Current implanted drug delivery systems are large and mostly cannot be placed local to the site that the drug is needed. Based on this disclosure, the implanted module can be injected into a targeted tissue region (for example, a tumor) where the drug is needed. The implanted module can include a number of drug reservoirs. The drug reservoirs can be activated by the external module via the patient/clinician user interface to release a drug into the targeted tissue region.

Temporary treatment. Currently, screening tests are typically performed before a permanent impulse generator is implanted. During the screening test, a patient may receive a temporary, external impulse generator. The generator can connect to an extension and a lead that are surgically placed in the body. In this period, the external impulse generator collects patient usage data and efficacy of the treatment. However, according to this disclosure, the implanted module having an electrode and an impulse generator can be injected into the targeted nerve/muscle region, eliminating the need for a temporary generator with leads. There is therefore no need for the external temporary impulse generator. In addition, this disclosure can also replace the temporary sensing and pacing leads used in patients after cardiac surgery.

Laboratory Experiments. The implanted module can be injected into lab animals or rodents (such as mice, rats, etc.) to monitor or sense parameters of the animal and/or provide stimulation to the animal in an experimental setting. The small size of the implanted module can advantageously provide opportunities to monitor the animal that has not been previously available. For example, the implanted module could be implanted on or near the brain of a rodent to monitor electrical signals of the brain. The implant can be wirelessly powered with the external module described above, and can be configured to communicate information back to the external module relating to the animal.

The devices are individually addressable and independently controlled. Thus, the devices, for example as those used for muscular stimulation, can be placed at different locations corresponding to different muscle groups, and perform stimulation in a synchronized manner.

Similarly, brain stimulation devices can be placed at different locations in the brain, and stimulation can be performed in a synchronized manner. The same can be said with drug delivery devices. Moreover, because the devices can be individually addressable and independently controlled, the devices can be activated and/or powered asynchronously as well as synchronously. These devices, in certain instances, can have characteristics dimensions in that the devices are much smaller (e.g., one, two, or three orders of magnitude) than their depth in tissue. Similarly, the devices, in certain instances, can have characteristics dimensions in that the devices are much smaller (e.g., one, two, or three orders of magnitude) than the source that provides the power to the devices.

The aspects of the present disclosure, as directed toward apparatuses, devices, and methods, can be utilized alone or in combination with various other aspects.

For information regarding details of other embodiments, experiments and applications that can be combined in varying degrees with the teachings herein, reference may be made to the experimental teachings and underlying references provided in the following attachments which form a part of this patent document and are fully incorporated herein by reference. Embodiments discussed in these appendices are not intended, in any way, to be limiting to the overall technical disclosure, or to any part of the claimed disclosure unless specifically noted.

In such contexts, these building blocks and/or modules represent circuits that carry out one or more of these or other related operations/activities. For example, in certain embodiments discussed above, one or more blocks and/or modules are discrete logic circuits or programmable logic circuits configured and arranged for implementing these operations/activities, as in the circuit modules/blocks described above and in the Appendices. In certain embodiments, the programmable circuit is one or more computer circuits programmed to execute a set (or sets) of instructions (and/or configuration data). The instructions (and/or configuration data) can be in the form of firmware or software stored in, and accessible from, a memory (circuit).

In connection with the above discussed features and illustrative figures, such structures can be used with sensors/devices that include feedback to the sub-wavelength structures. These types of sensors can include, for example, implantable temperature sensors or imaging devices.

In this manner, the devices are responsive to the structures illustrated above that generate a spatially adaptable electromagnetic field/signal. The feedback-type devices respond to the power and/or data portions of the signal provided by the spatially adaptable electromagnetic field/signal, and are prompted to respond. For instance, temperature sensors located in a patient will broadcast/report the temperature of the tissue in response to the power and/or data portions of the signal provided by the spatially adaptable electromagnetic field/signal. Additionally, imaging devices implanted in a tissue can broadcast/report the captured images in response to the power and/or data portions of the signal provided by the spatially adaptable electromagnetic field/signal. Moreover, the penetration depth of the spatially adaptable electromagnetic field/signal can be modeled and controlled. Thus, in certain embodiments, the feedback devices can indicate and label data, in response to the spatially adaptable electromagnetic field/signal, to record the depth at which the device is operating. By storing this data on a patient-by-patient basis in a storage device, a computer can access and analyze this data for statistical purposes.

By storing the position or label of the feedback-type device in a memory circuit via a programmable computer, various patient feedback tracking methods can also be realized. For instance, the depth of an implantable imaging device can be optimized by analyzing the surrounding tissue. In this manner, the depth of the implantable imaging device can be adjusted if it is determined that a more optimal position is possible. Similarly, the depth of an implantable stimulation device can be used to determine the heath of the tissue area surrounding the stimulation device, and determine an optimal positioning of the device in response to the spatially adaptable electromagnetic field/signal. Additionally, the feedback-type devices can respond to the spatially adaptable electromagnetic field/signal and broadcast data stored in a memory circuit. Thus, the feedback-type devices can continuously update a physician of the data that is being tracked by the device. This allows for real-time monitoring, diagnosing, and/or treating a patient wirelessly.

Wireless Powering for Catheter-Insertable Electronics

Seamless integration of electronics into the body can restore and augment many physiological functions. However, its realization is restricted by the enormous mismatch in scale between the microscopic (nanometers to millimeters) integrated electronics and macroscopic (centimeters) energy storage or harvesting components. Here, we introduce midfield wireless powering, which we validate to be capable of powering a 2-mm active device 10 cm deep in tissue three orders of magnitude reduction in size with a tenfold increase in depth over conventional approaches. The powering source is realized through a patterned metal plate that excites propagating waves in tissue from its evanescent components, and generates a focused and spatially adaptive electromagnetic midfield. To illustrate the capabilities of this approach, we built a 2-mm diameter, 70-mg wireless pacemaker and demonstrated closed-chest wireless pacing.

We report power transfer to miniaturized semiconductor devices by exploiting propagating waves in biological tissue generated in the midfield electromagnetic region of the source. At the scale of a millimeter, wireless devices must operate at depths in dissipative tissue that are over an order of magnitude greater than their characteristic sizes. In such configurations, established mechanisms for free-space transfer are highly inefficient: near-field approaches, which rely on strong coupling occurring between objects with matched electrical characteristics such as resonances and impedances, do not generalize easily to geometries with extreme size asymmetry, while far-field transfer is limited by absorption over surfaces of the body. Although energy sources based on thermoelectric, piezoelectric, biopotential, or glucose harvesting are promising alternatives, they do not in their existing forms (<0.1 µW/mm$^2$) achieve power densities sufficient for a millimeter-sized device. Powering in the midfield provides a different approach in which both evanescent and radiative components of a structure are coupled to modes in tissue that transport energy continuously away from the source. Interference resulting from phase differences between these components affords additional opportunity for spatially focused and dynamically adjustable field patterns inside tissue.

We demonstrate systems that exploit these characteristics to wirelessly power miniaturized devices—sufficiently small to be delivered by a catheter —inserted several centimeters in heterogeneous tissue. For many classes of electronics, the level of performance obtained by this approach exceeds requirements for advanced monitoring and control capabilities that might be developed for applications in medicine, neuroscience, or human-machine interfaces.

We identify the physics underlying the midfield by considering power transfer through a multilayer approximation of the chest wall. The powering configuration consists of a source positioned above the skin and a receive coil inserted in the cardiac tissue layer (FIG. 1A). The layered structure permits a simple description of wave propagation while providing some physical resemblance to surfaces on the body. Power transfer occurs when the interaction of the source fields with the coil structure results in work extracted by a load in the receiver circuit. For a subwavelength coil, only the lowest order mode is important and the transfer mechanism can be described by electromagnetic induction characteristic of dynamic magnetic field interactions. In this case, the power transferred from the source to the coil is given by $$P_{SC} = \int d^3 r M_C(t) \cdot \frac{dB_S(t)}{dt} \quad (1)$$

where Bs is the magnetic field generated by the source and Mc the induced magnetization due to current in the coil.

The electric and magnetic fields generated by a time-harmonic current density Js on sur-face of the source conductor can be solved by decomposing the current density into its spatial frequency components (kx, ky). Each component corresponds to a plane wave with propagation determined by phase matching conditions for refraction and reflection over planar boundaries, from which the total field in tissue can be recovered at each depth z by an integration over the source spectrum. Using phasor notation with a time dependence of exp(-iwt), we can define an efficiency in terms of these fields $$\eta = \frac{\left| \int d^3 r M_C^* \cdot B_S \right|^2}{[\int d^3 r \text{Im} \in (\omega)|E_S|^2][\int d^3 r \text{Im} \in (\omega)|E_C|^2]} \quad (2)$$

Formally, η is the ratio of power available at the coil to the total absorbed power. Eq. 2 considers only dissipation in tissue: other losses, such as radiative and ohmic loss, arise in practice, but the amount of power that can be coupled into the body is essentially limited by electric field-induced heating in tissue. Efficiency as defined above is intrinsic to the fields in the tissue half-space and gives an upper bound on the efficiency that can be obtained. The work extracted by the load can be determined by impedance matching considerations and other implementation dependent factors.

The choice of source Js that maximizes efficiency in Eq. 2 is key for efficient power transfer. Direct search over the space of such candidate current densities, however, is not feasible because it leads to intractable computational complexities. Approaches to related problems, such as the design of optical antennas, rely on non-global optimization strategies (e.g. genetic algorithms) that find locally optimal structures. We developed an alternative method that enables the global optimum to be analytically solved, although in terms of a non-physical current density, for a specified powering configuration. In this approach, an electric current density is defined with components tangential to a plane between the source structure and the tissue. For every source, the electromagnetic equivalence theorem enables such a two-dimensional current density to be chosen from the overall set S that is indistinguishable in the lower z<0 half-space from the physical source of the fields. Remarkably, a solution to the optimization problem maximize Js∈S η (Js) can be found in closed-form as a consequence of the simple vector space structure of S. Unlike solutions derived from local optimization algorithms, the maximum efficiency obtained by this procedure is a rigorous bound on the performance that can be achieved by any physical realization of the wireless powering source.

Figure 9A:
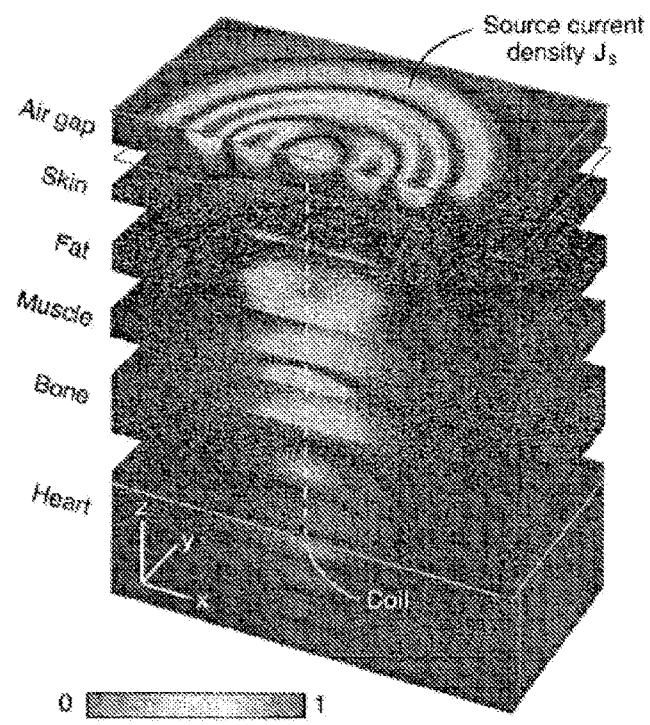
FIGS. 9A-9E show a multilayer model of power transfer.
Figure 9B:
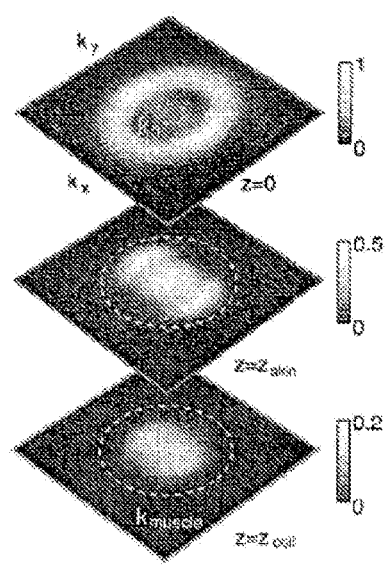
Figure 12:
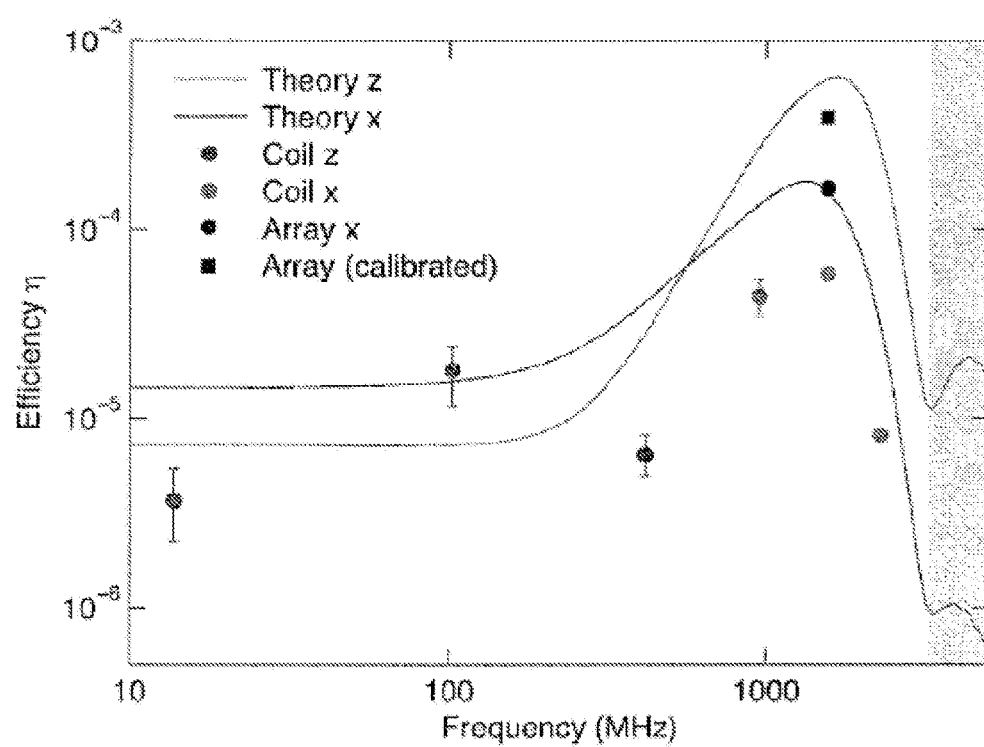
FIG. 12 shows a power transfer efficiency chart.

By exploring such global solutions across a range of frequencies with appropriate dispersion models for biological materials, we were able to establish optimal power transfer for the chest wall structure. For a 2-mm diameter coil inserted at a 4 cm depth in tissue with its magnetic dipole moment aligned with the x axis to maximize coupling with a transverse magnetic field component, the optimal frequency occurs near 1.6 GHz where the tissue wavelength (λ ≈2 to 4 cm) is comparable to the powering distance (FIG. 12). The properties of this midfield region are key to optimal powering, as the resultant magnetic field in FIG. 9A shows. The fields consists of propagating waves (alternating electric and magnetic fields) that converge on the device. Back-propagation of fields at the focal plane to the surface of the skin reveals that the source is highly oscillatory and composed of significant evanescent components $\sqrt{k_x^2+k_y^2}>k_0$ that are important only in the near-field (FIG. 9B). In contrast with conventional near-field powering (FIG. 1C), however, these evanescent components excite propagating modes in tissue that transport energy to absorption-limited depths. Although far-field methods also exploit such propagating waves, they only involve $\sqrt{k_x^2+k_y^2}>k_0$ components that do not provide similar spatial confinement of electromagnetic energy (FIG. 1D). The amplitudes and phases of the components emerging from the optimization solution are designed such that their superposition is focused at a device plane. The requisite near-field characteristics (FIG. 1E) are unlike those of dipole or coil primitive elements, requiring more complex electromagnetic structures for synthesis.

Figure 9C:
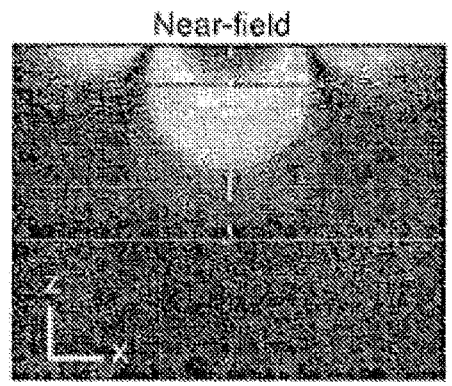
Figure 9D:
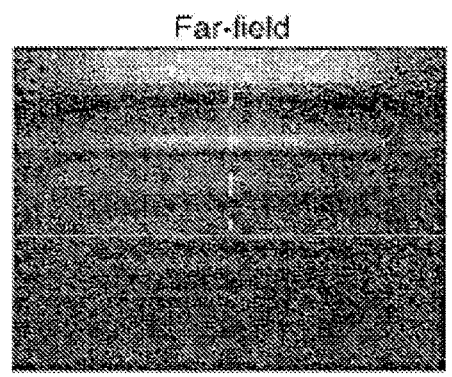
Figure 9E:
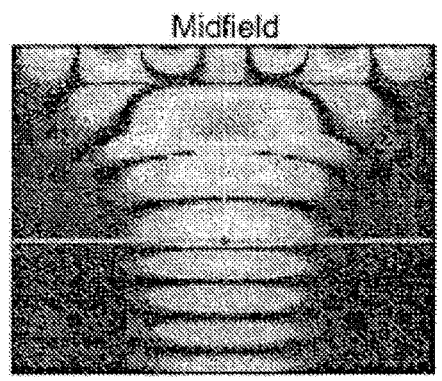

FIGS. 9A-9E show a multilayer model of power transfer to a subwavelength coil in tissue. FIG. 9A shows a schematic of midfield power transfer in a multilayer tissue structure. The magnetic field (Hx, linear scale) corresponding to the analytically derived optimal source current density Js (f=1.6 GHz, $Z_{skin}$=−1 cm, $Z_{coil}$=−5 cm) is shown; the receive coil is oriented in the x direction. FIG. 9B shows spatial frequency spectra at specified depth planes. $k_0$ is the wavenumber corresponding to propagation in air; $k_{muscle}$ the wavenumber in muscle tissue. FIG. 9C shows a magnetic field generated by conventional near-field power transfer (Hz, logarithmic scale, f=10 MHz). FIG. 9D shows a magnetic field generated by far-field power transfer calculated by removing the evanescent components in FIG. 9B (Hz, logarithmic scale). FIG. 9E shows a cross-section view of FIG. 9A (Hz, logarithmic scale). FIGS. 9C to 9E are normalized such that the maximum electric field in tissue is the same.

Near-perfect efficiency, while possible for mid-range systems with large and symmetric coils, is not necessary for realizing wireless capabilities. Many classes of low-power integrated circuits incorporate functions such as communication, sensing, and stimulation in devices consuming less than 20 pW during active operation. In the present numerical example, the theory indicates that up to 320 µW can be transferred to the load if the source couples 500 mW, roughly the power radiated by a cell phone, into the chest ($\eta \approx 6.4 \times 10^{-4}$). The efficiency of power transfer is one to two orders of magnitude greater than that of near-field systems in similar configurations, which are less than $10^{-5}$ due to weak coupling. The latter performance is generally not sufficient for operation in close proximity to tissue —safety and complexity considerations limit the power flowing through the external source circuitry (<2-10 W depending on frequency)—but such requirements can be met with the above theoretical transfer characteristics.

Figure 10A:
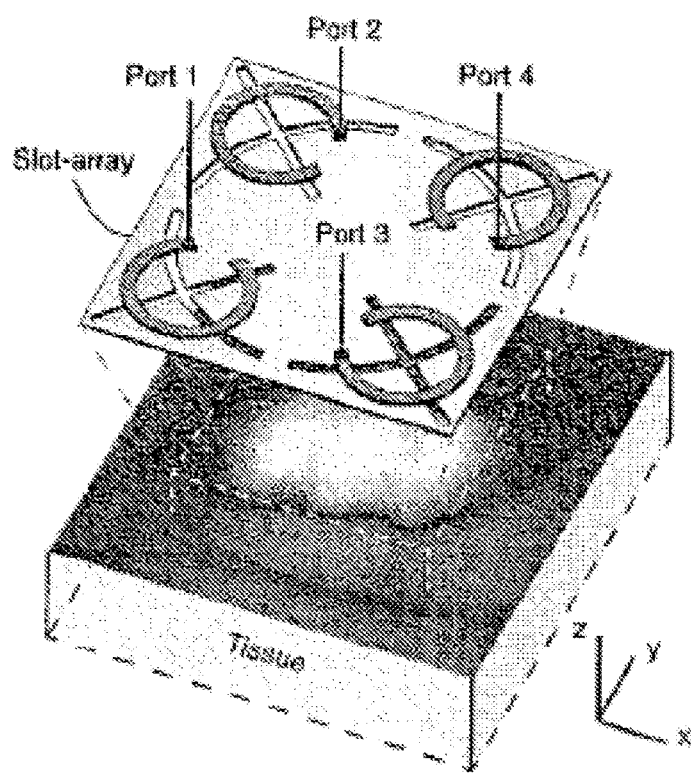
Figure 10B:
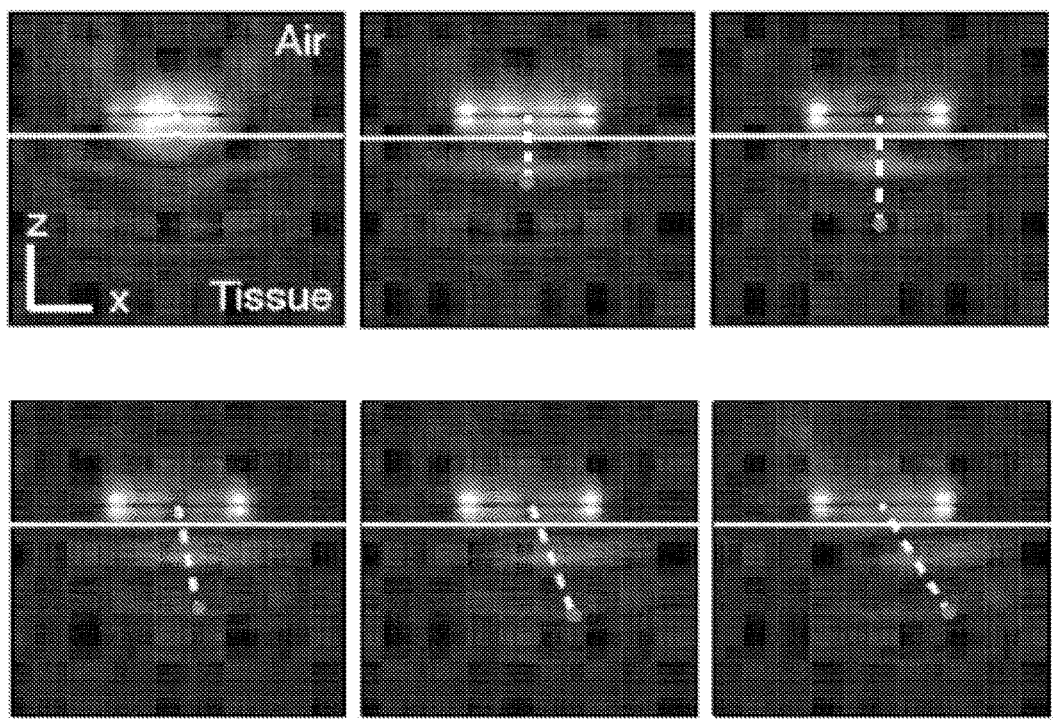

FIGS. 10A-10G show midfield power transfer realization with a patterned metal plate. FIG. 10A shows a schematic of the source design (dimensions 6 cm×6 cm, operating frequency 1.6 GHz) and the magnetic field $H_x$ over the skin surface. FIG. 10B shows field patterns with spatially shifted focal points designed by adjusting relative phases between the port signals. The upper diagrams in FIG. 10B show formation of the propagating wave in a direction directly below the external module. The lower diagrams in FIG. 10B show adjustment of the focal point of the wave, and thus the direction of the wave. As described, this adjustment can be attained by adjusting a phase and/or amplitude of the sub-wavelength structures of the external module.

Figure 10C:
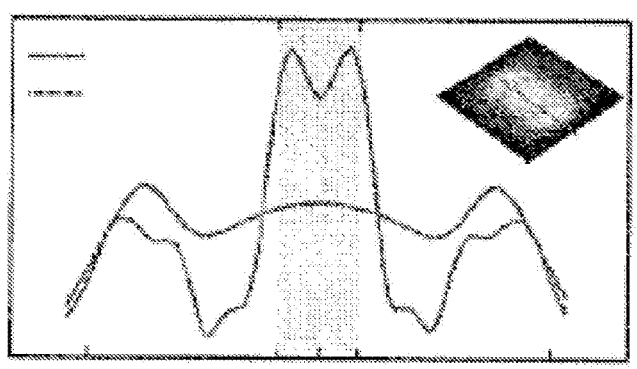

FIG. 10C shows spatial frequency spectrum along the $k_x$ axis for the magnetic field in FIG. 10A compared with the theoretical optimum. FIG. 10D shows an experimental setup for power transfer measurements. FIG. 10E shows theoretical, numerically simulated, and measured power received by a 2-mm coil when coupling 500 mW into a liquid solution mimicking the dielectric properties of muscle tissue. FIG. 10F shows a strobed position of the LED as the wireless device moves in a "S" shaped trajectory. A real-time control algorithm enables dynamic focusing while the device is in motion. FIG. 10G is the same as FIG. 10F but without dynamic focusing; the field pattern is static and focused at the center.

Our physical realization of the midfield powering source consists of a metal plate patterned with slot structures and excited by four independent radio-frequency ports (FIG. 10A). For appropriate phases between the port signals, the slot-array structure generates circular current paths that mimic the optimal current density. When positioned above tissue, the structure couples power from the external circuitry into the tissue volume with high efficiency (>900/%), as evidenced by both low levels of backside radiation (FIG. 10B) and a pronounced minimum in the scattering parameter spectrum (FIG. 11).

Figure 11:
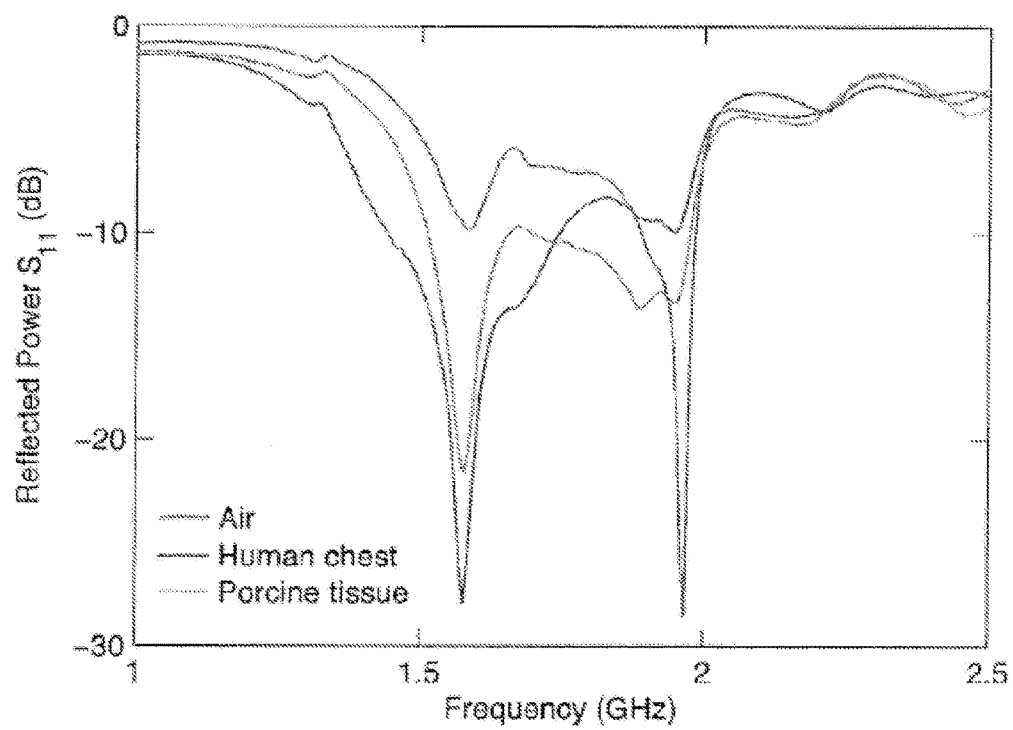
FIG. 11 shows a reflected power spectrum as a function of frequency.

FIG. 11 shows a reflected power spectrum $S_{11}$ as a function of frequency measured at an input port of the slot-array source. When positioned 1 cm above the human chest or porcine tissue, a pronounced dip is observed at the design frequency 1.6 GHz. Since backside radiation is negligible, electrical power from the signal generator is efficiently coupled to propagating waves in tissue. At a higher operating frequency 1.9 GHz, power is efficiently coupled into waves in air. The structure behaves as a conventional radiative antenna in this region.

Analysis of the fields on the surface of the skin shows that the evanescent spectrum approximates the theoretical optimum (FIG. 10C), although the contribution of the radiative modes are about a factor of two greater owing to the inherent directionality of the planar structure. Regardless, when transferring power to a device submerged in a 0.5% saline solution with dielectric properties mimicking muscle tissue, experimental and numerical studies show that the design obtains efficiencies within 10% of the theoretical bound (FIG. 10E).

Degrees of freedom provided by the phases of the input port signals enable various interference patterns to be synthesized, including those with spatially shifted focal regions (FIG. 10B). Software control of these phases can refocus the fields without mechanical reconfiguration, which could be useful for probes inserted on rhythmic organs or for locomotive devices. We implemented a "greedy" phase search algorithm based on the closed-loop feedback relayed over an fiber optic cable (FIG. 10D) that obtains focusing-enhanced power transfer in real-time. Over a "S" shaped trajectory of motion, this adaptation eliminates the outage regions that occur in the static case (FIG. 13), indicating a coverage area much wider than that intrinsic to the focal region (FIGS. 10F and 10G). Incorporating components for wireless communication in the device will enable an untethered realization of this and other related control algorithms.

Figure 13A:
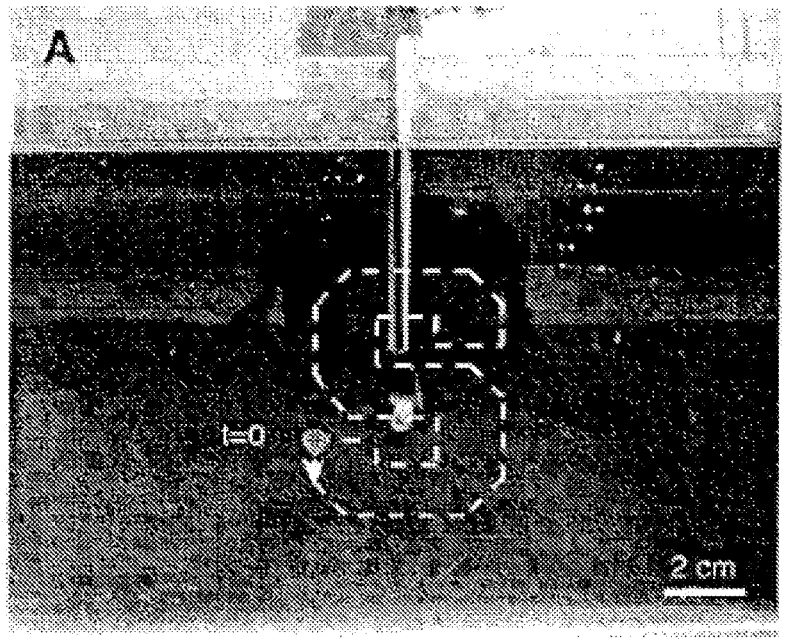
FIGS. 13A-13D show an example of device movement.
Figure 13B:
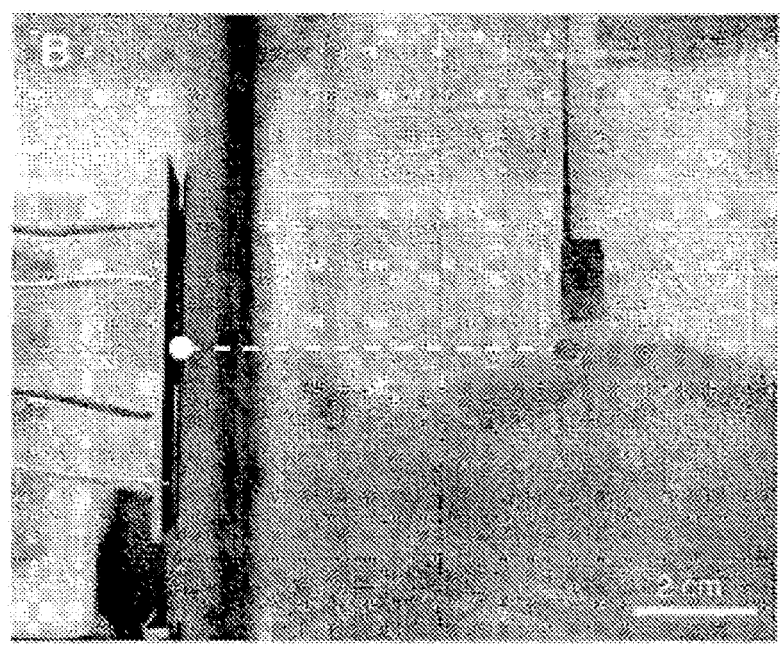
Figure 13C:
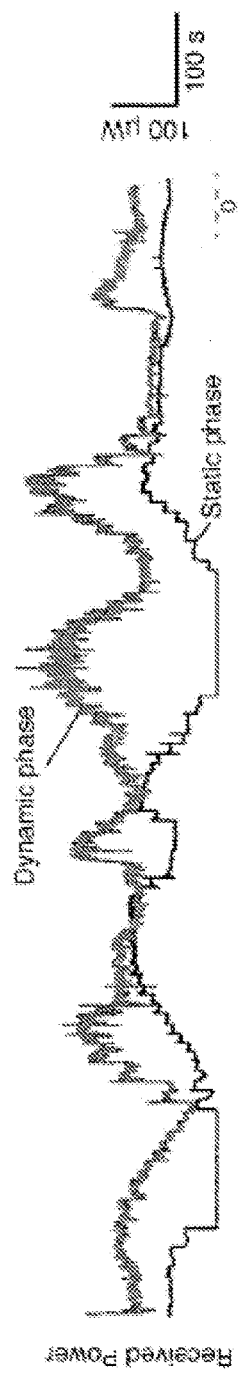
Figure 13D:
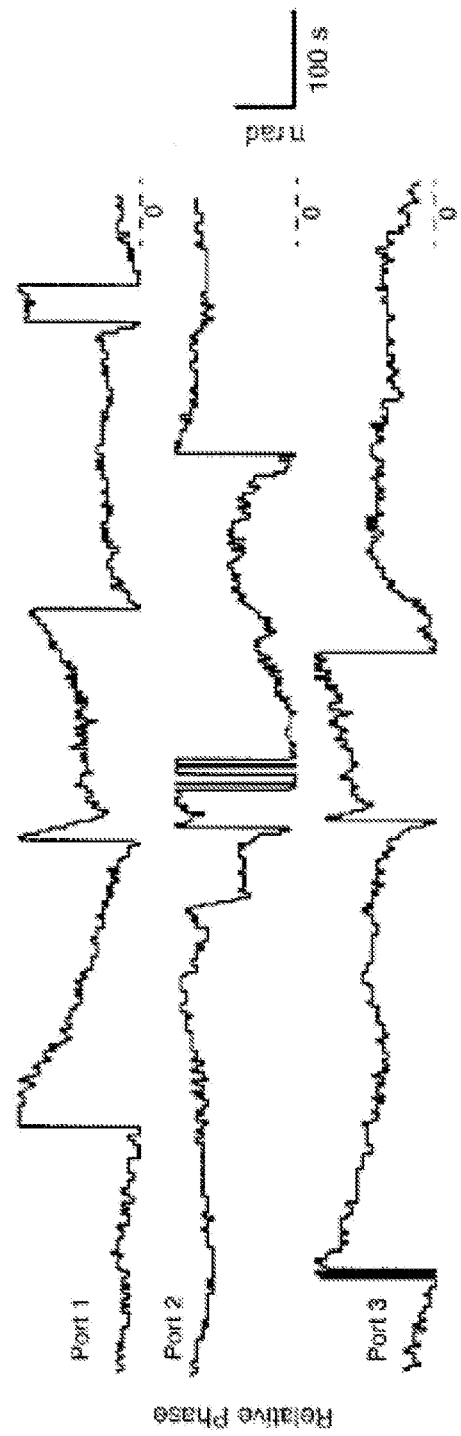

Received power and array phases as the device moves along the "S"-shaped trajectory. FIG. 13A shows a trajectory of the device in a liquid solution with dielectric properties imitating muscle tissue. The dot marks the starting position. FIG. 13B shows separation between the device (dot) and the center of the source (white dot). The distance is approximately 6 cm, including a 1 cm air gap between the source and the liquid. FIG. 13C shows power received by the device measured by the flashing rate of the LED. The minimum power to operate the device is about 10 pW. The dynamic phase adaptation algorithm enables higher levels of power to be transferred as the device moves. FIG. 13D shows a phase of each port, relative to a phase stationary port 4, controlled by the algorithm along the trajectory of motion.

Figure 14A:
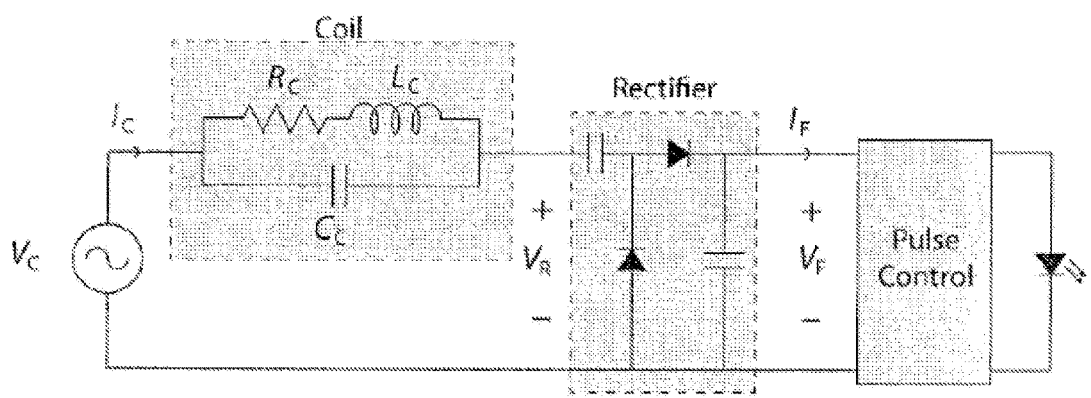
FIGS. 14A and 14B show schematics of a power measurement probe.
Figure 14B:
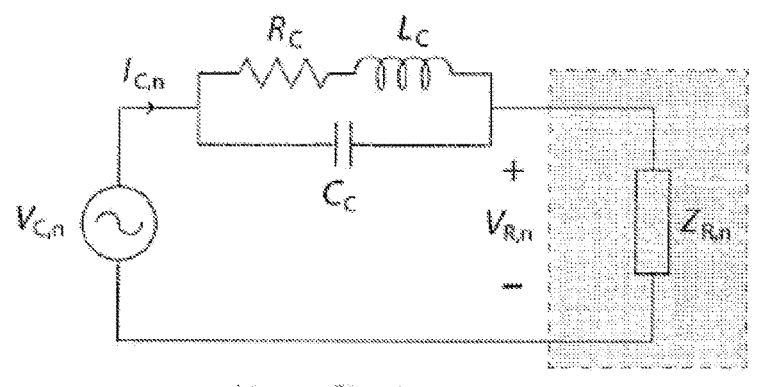

Relative to a millimeter-sized coil, probes based on conductive wires interact strongly with the source fields, making them unsuitable for measuring the transferred power. We instead developed an integrated probe that separates the powering and measurement modalities by encoding the electrical power level into the frequency of optical pulses. The probe consists of a multi-turn coil structure, rectifying circuits for AC-DC power conversion, a control unit for regulating the pulse amplitudes, and a light-emitting diode (LED) (FIGS. 14A and 14B). A fiber optic cable guides the signal to a terminating photodiode at the measurement location. We are able to calculate the power transferred to the coil, calibrated for circuit-dependent inefficiencies, by recording the end-to-end power levels at multiple reference flash rates. From the non-linear response of the circuit, a system of linear equations can be solved to yield the wireless power transfer efficiency in Eq. 1.

We evaluate the performance of our powering scheme in complex tissue geometries by designing two configurations that simulate power transfer to devices in the left ventricle of the heart and the cortex region of the brain in a pig. The source and device positions within the tissue volume using magnetic resonance imaging (MRI) reconstructions, are separated by at least 4 cm of heterogeneous tissue. When coupling 500 mW into tissue, we estimate the power transferred to the coil to be 195 µW for the heart and 200 µW for the brain configurations. The overall efficiency, inclusive of all subsequent circuit losses, is about a factor of two less, depending on environmental loading effects: we measured the respective powers flowing through the pulse control units to be 90 µW and 82.5 µW. Most of the intermediate losses are due to inefficiencies in power conversion and can be expected to be substantially reduced with improved rectifier designs.

To determine the spatial distribution of absorbed energy, we operated the source over an extracted piece of tissue and measured surface changes in temperature. Infrared imaging shows about a maximum 1.7° C. increase when 500 mW is continuously coupled into tissue over a period of 1 hour. The heating in live subjects is expected to be substantially less because of additional mechanisms for thermal regulation. From the initial rate of change in temperature, we estimate that the peak specific absorption rate (SAR) is 3.9 W/kg in the volume directly under the source. As a cross-check, this value can be compared to the peak SAR that occurs when the same amount of power is coupled into a multilayer tissue structure. We numerically calculate the SAR to be 3.5 W/kg, which is within 15% of the experimental estimate. Although the measured absorption exceeds that of cell phones, it is approximately a third of the threshold for controlled environments and remains well below other levels specified in medical guidelines, such as those for MRI. If the power coupled into tissue is allowed to meet the maximum permitted level of exposure (<10 W/kg over any 10 g of tissue), we estimate that ~190 µW/mm$^2$ can be transferred. The low average absorption (<0.04 W/kg for adult humans) and highly localized distribution suggests that the power transfer is unlikely to have a meaningful impact on core body temperatures.

The power transfer configurations evaluated here suggest that millimeter-scale electronics can be operated at distances sufficient for insertion at nearly arbitrary locations in the body. Integration with existing MEMS, logic units, sensors, light sources, and other components will yield many other capabilities, such as wireless communication or mechanical actuation. Applications that may emerge on this scale include distributed sensors for the heart, deep-brain neural probes, and locomotive transports in the bloodstream.

Materials and Methods

Numerical methods. The fields shown in FIGS. 9A-9E of the main text were calculated from the spectral components of an in-plane source current density Js (kx, ky) using the dyadic Green's function method. This method reduces to a simple transfer function because the plane-wave components are eigenfunctions of propagation in the multilayer structure. At each depth z, for example, we apply a dyad $G_H$ ($k_x$, $k_y$, z) to calculate the magnetic field H ($k_x$, $k_y$, z)=$G_H$($k_x$, $k_y$, z)Jc($k_x$, $k_y$). An inverse Fourier transform yields the fields at each depth. The fields in FIGS. 10A and 10B of the main text were calculated using a commercial electromagnetic simulator (CST Studio Suite, CST). The slot-array structure was placed above a tissue multi-layer (1 cm air gap, 4 mm skin, 4 mm fat, 4 mm muscle, 16 mm bone, 144 mm heart) and the fields calculated by a time-domain solver. A similar simulation setup—with tissue layers simplified to a slab with the dielectric properties of the liquid solution (0.5% saline)—was used to obtain the simulation curve in FIG. 2E. The port phases were reconfigured at each depth to maximize power transfer.

Theoretical power transfer calculations. The theory curve in FIG. 10E was calculated by considering optimal power transfer to a 2-mm coil in an air-muscle half-space at varying distances (2 to 10 cm, with a 1 cm air gap). At each depth, the optimal source Js was solved, from which |κ|/Γs was calculated from the resultant fields Es and Bs. The remaining parameter $\Gamma_C$ was experimentally estimated using the efficiency calibration procedure. Theory curves in FIG. 12 were obtained in a similar manner except that an analytical solution for the fields due to a single loop of wire in homogenous heart tissue (via boundary conditions of its spherical harmonic components) was used to estimate $\Gamma_C$. Experimental estimation was not possible across the entire frequency range because of numerical instabilities when $\Gamma_C \ll 1$.

FIG. 12 shows efficiency of power transfer to a 2 mm diameter coil at a range of 5 cm as a function of the operating frequency. Theoretical efficiency generated by solving for the optimal η for a multilayer model of the chest wall (solid lines). Power transfer with the z component of the magnetic field (Theory z) is advantageous at low-frequencies where the receiver is in the near-field; in the mid-field, the transverse x component of the magnetic field is dominant (Theory x). Measured end-to-end efficiencies for six coil-based sources, designed to operate at points across the frequency range 10 MHz to 4 GHz, for the porcine brain configuration. The error bars show fluctuation in efficiency due to circuit nonlinearities as the receiver end power level varies from ~10-40 µW. Peak end-to-end efficiency (dot) of the slot-array structure and power transfer efficiency, calibrated for circuit inefficiencies (black square). The coil's self-resonance frequency occurs at about 3.2 GHz beyond which higher order modes of the coil may contribute (shaded area).

Electromagnetic region of operation. The frequency of operation was selected to maximize the efficiency of power transfer to a 2-mm diameter coil at a range of 5 cm (with a 1 cm air gap). Theoretical efficiency versus frequency curves (FIG. 12) were generated by solving for the optimal q in a multilayer model of tissue (1 cm air gap, 4 mm skin, 4 mm fat, 4 mm muscle, 16 mm bone, ∞ heart) across a wide frequency range (10 MHz to 4 GHz) for coils oriented in the x and z directions, where the upper limit is selected to be about the self-resonance frequency of the coil. Coil losses were calculated using an analytical model for a loop of wire embedded in uniform tissue and impedance matching performed with the constraint Q<10 where Q is the quality factor. Using the Dehye dispersion model for each tissue type, the peak efficiency was found to occur at 1.6 GHz. Since each efficiency is the maximum that can be obtained by any implementation of the source, we conclude that this is the optimal frequency of operation.

To experimentally validate the result in a complex tissue structure, we designed six coil-based source and receiver structures operating in the frequency range (13, 102, 416, 950, 1560, and 2280 MHz). Each source-receiver pair represents a "best effort" attempt to achieve efficient power transfer in their respective electromagnetic regions. FIG. 12 shows that the measured end-to-end efficiencies replicate the general shape of the curve. The peak realized efficiency is observed at 1.6 GHz among the coil-based sources, with about a factor of 3 enhancement provided by field focusing with the array structure. Calibrating for circuit inefficiencies, the experimental efficiency of power transfer is found to be within 40% of theory, although the composition of the intermediate tissue is highly dissimilar.

Probe trajectory visualization. A power measurement device was attached to the end of a fiber optic cable and submerged in a liquid solution (0.5% saline). A custom-built 3D positioner (LEGO Mindstorms) moved the device in a "S" shaped trajectory. A photo sequence was obtained in a dark room with ½ s exposure every 5 s while the device was in motion. The entire "S" shaped path was completed in 20 min. The composite image was created by thresholding the brightness of each image and superimposing the result.

Tissue imaging. Magnetic resonance imaging (MRI) of porcine tissue was performed at the Stanford Magnetic Resonance Systems Research Lab (MRSRL). A T2-weighted spin-echo pulse sequence was used for the heart and chest; T2-weighted fast spin-echo was used for the head. Reconstruction was performed with the OsiriX software package.

Thermal imaging. Explanted porcine loin tissue, brought approximately to room temperature, was used for the heating experiment. The slot-array source was placed 1 cm above tissue and configured to couple 500 mW into tissue with uniform phase settings. Air flow between the source and the tissue was minimized by using a foam spacer. The source was briefly removed (<3 s) at each time point to allow infrared imaging of the tissue surface (FLIR Thermal Imaging i7). An experimental control, extracted from the same tissue piece, was placed in the field of view of the camera. An estimate of the overall change in temperature was obtained by observing the hot spot and subtracting uniformly from the measured change in background temperature. Infrared imaging of the surface of the metal plate showed no detectable heating.

Safety considerations. We refer to IEEE guidelines for safety thresholds, although it should be noted that they are not intended for medical applications. Since our scheme relies on the coupling of both evanescent and radiative components into tissue, thresholds based on incident power densities are not adequate. Relevant measures are instead provided by the specific absorption rate (SAR), defined as the power loss integral over a reference volume. The standard includes two relevant SAR thresholds: one averaged over the whole body (<0.4 W/kg) and another for partial body exposure (<10 W/kg, averaged over any cube-shaped 10 g of tissue). Our scheme is clearly compliant to the whole body average —when coupling <2 W into the body, the SAR about an order of magnitude less than the threshold (<0.04 W/kg) for a typical adult human (60 kg).

Determining the partial body exposure requires estimation of the spatial distribution of absorbed energy. Following recommended procedures, SAR was calculated from the initial slope of the temperature change curve $SAR=C_p(\Delta T/\Delta t)|_{t=0}$ where $C_p$ is the specific heat capacity and $\Delta T$ the change in temperature over an exposure duration of $\Delta t$, selected such that thermal conduction and convection effects are negligible. For porcine tissue, the heat capacity is approximately $C_p=3140$ J/kg K, yielding an estimated SAR of 3.9 W/kg. Although the output power is comparable to cell phones, the measured absorption is greater (>2 W/kg) because, unlike cell phones, almost all of the power is coupled into tissue. The SAR nevertheless remains well below the 10 W/kg limit for controlled environments. As a cross-check, power loss densities in a multilayer tissue structure were also numerically calculated using a commercial solver (CST Studio Suite, CST). When a total of 500 mW is dissipated in tissue, the maximum SAR, averaged over 10 g of tissue (or approximately cubes of side length 2.15 cm), was found to be 3.5 W/kg. Based on these values, we estimate that we can couple up to 1.43 W into tissue before the 10 W/kg threshold is exceeded.

Figure 15A:
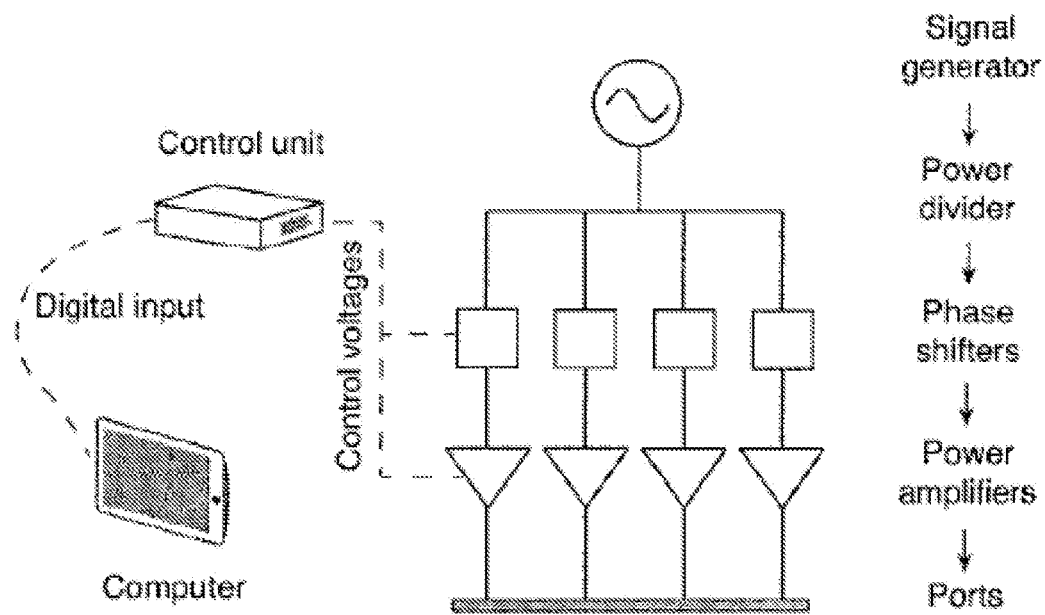
FIGS. 15A and 15B show slot-array control components.
Figure 15B:
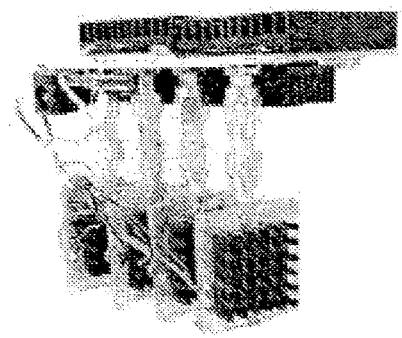

Source design. The slot-array source realization consists of a patterned metal structure excited at four ports with RF signals of controlled phases (FIGS. 15A, 15B, and FIG. 10A). The patterned metal plate was fabricated on a 1.6 mm FR4 substrate with feed and pattern copper layers. Semi-rigid coaxial cables were used to connect each excitation port to the control board. A RF signal at 1.6 GHz was brought from the signal generator to the control board and then separated into four signals using a Wilkinson power divider. Following power division, the signals are connected to parallel stages for variable attenuation, phase shifting, and amplification. The phase shifters are voltage controlled and adjusted using a NI 9264 compactDAQ module (National Instruments) via LabVIEW (National Instruments).

FIGS. 15A and 15B show slot-array control components. FIG. 15A shows a schematic of excitation and control of the slot-array realization of the power transfer source. When feedback from the device is available, independent control of the phase shifters enables dynamic adjustment of the interference pattern in tissue. FIG. 15B shows a slot-array implementation consisting of two circuit boards containing the power divider and four parallel phase shifters and power amplifiers.

Probe design. The probe consists of a receiving coil, rectifier, charge pump, flash control integrated circuit, and an LED (FIGS. 14A and 14B). The coil was wound with an inner diameter of 2 mm using copper wire (200 um diameter), with variable number of turns (between 1 to 15) depending on the design frequency. For the rectifier circuit, two Schottky diodes (Skyworks SMS7630 series) and two 10 nF capacitors were arranged in a charge pump configuration. At low frequencies, an additional capacitor was used in order to match the impedance of the coil and the rectifier. A charge pump and flash control integrated circuit was placed after the rectifier for up-converting the rectified voltage to the 2.0 V necessary to drive the LED. Charge was stored on a discrete 4.7 µF capacitor, and discharged through the LED (ROHM PICOLED) when a specified threshold voltage was reached. The entire probe was encapsulated in epoxy, connected to a fiber optic for power information readout. The minimum power to operate the device is about 10 µW. All components were bonded to a printed circuit board of Rogers 4350 substrate.

FIGS. 14A and 14B show circuit schematics of the power measurement probe. FIG. 14A shows a lumped circuit model of the receiver used to measure power transfer. An AC voltage Vc is generated across the coil by the source fields. The rectifier circuitry performs AC to DC power conversion the power flowing is encoded into the flashing frequency of the LED though the pulse control unit. FIG. 14B shows an equivalent circuit at the nth reference power level. The non-linear properties of the rectifier and pulse control unit enables the unknown parameter $R_C$ to be estimated by characterizing the circuit at two reference flashing frequencies.

Efficiency calibration. The efficiency of power transfer was experimentally measured with the probe. In order to calibrate for the intermediate circuit losses, which are substantial (>50%) in the design, the non-linear behavior of the circuitry was exploited to form a set of linearly independent equations from which unknown coil parameters can be solved. This system of equations was obtained by considering the circuit in FIG. 13A. Here, we represent the coil by an inductance $L_C$, in series with a resistance RI and a voltage source $V_R$ (originating from the induced emf), where the latter two parameters are unknown. From electromagnetic theory, the resistance can be identified as $R_C = 1/|I_C|^2 \int d^3 r \, \text{Im} \in (r)|E_C(r)|^2$. This quantity is identical to the coupled-mode parameter re, aside from a normalizing constant, and contains the integral appearing in the denominator of Eq. 1.

We characterized the non-linear circuit at two reference pulse rates, $r_1$ and $r_2$, by finding the corresponding pseudo-impedances $Z_{R,n} := V_{R,n}/I_{R,n}$. In general, the $Z_{R,n}$ are not equal because of non-linearities in particular circuit components. The corresponding amplitudes $I_{R,n}$, and $V_{R,n}$ were found through harmonic balance analysis using commercial circuit design tools (Advanced Design Systems, Agilent). From the reduced model in FIG. 13B, we obtained the following equations by a straightforward application of Kirchoffs voltage law: $V_{C,n} = (R_C + Z_{R,n})I_{C,n}$ for n=1,2. The two equations are linearly independent if the reference rates correspond to operation in a non-linear region of the circuit.

For each powering configuration, an additional equation was obtained by adjusting the power level at the source until the observed pulse rate equals $r_1$ and $r_2$. Recording the two reference levels $P_{s,1}$ and $P_{s,2}$, an additional equation $V_{C,2}/V_{C,1} = \sqrt{P_{S,2}/P_{S,1}}$ was obtained, permitting the unknown parameters VC,n and RC to be easily solved. The efficiency was then found by directly calculating $\eta = |V_{C,n}|^2/8R_C P_{S,n}$.

Cardiac pacing. Adult New Zealand White Rabbits (3.0-4.0 kg) were used in the cardiac pacing study. All animals were housed in individual cages in the large animal facility. They were allowed to acclimatize to the holding facility for five to seven days before the procedure was conducted. All animals were given access to food pellets, hay and water ad libitum and maintained on a 12 hour light-dark cycle (lights on at 7:00 AM). All animals were fed a normal diet throughout the experimental period.

The surgical site was shaved using clippers followed by a surgical scrub alternating between alcohol and Betadine. A gauze sponge was used for scrubbing. All through the procedure, draping of the surgical area was done appropriately. The operative procedure was performed with aseptic technique. Surgery was performed under general anesthesia (ketamine; 35 mg/kg, xylazine; 5 mg/kg, i.m. injection) using sterile technique. Antibiotics (cephazolin 20-30 mg/kg) were administered intravenously to the animal prior to surgery. Anesthesia was maintained with endotracheal intubation and inhaled isoflurane (~2.5-3.0%/).

Once confirmed that the animal was completed sedated, a surgical incision was made. A vertical midline incision was made and sternotomy was performed using aseptic conditions. The pericardium was excised to expose the heart. Once the heart was in position, a 2 mm pacemaker device was inserted into the apex on the heart. The total procedure time was 15 minutes.

The rabbits were sacrificed using an overdose of sodium pentobarbital (200 mg/kg, i.v. injection). Prior to that, Ketamine 20-40 mg/kg SQ and Xylazine 2-5 mg/kg/SQ was administered to put the animal to sleep. All procedures were approved by the Animal Care and Use Committee of Stanford University.

Efficiency of Power Transfer.

The expression for efficiency in Eq. 2 above can be derived using coupled mode theory. In this formalism, the exchange of energy between the source and receiver is described by the equations $$\dot{a}_S(t) = (i\omega_S - \Gamma_S)a_C(t) + \kappa a_S(t)$$

$$\dot{a}_C(t) = (i\omega_C - \Gamma_C - \Gamma_L)a_C(t) + \kappa a_S(t)$$

where $a_n$ are amplitudes normalized such that $|a_n|^2$ corresponds to the energy in the structure, $\Gamma_n$ the intrinsic decay rates, $\Gamma_L$ the rate of work extraction by the load on the receiver, and $\kappa$ the coupling coefficient. It may be advantageous to operate with the source and receiver in resonance $\omega = \omega_S = \omega_C$. The efficiency of power transfer is defined as $$\eta' = \frac{\Gamma_L |a_C|^2}{\Gamma_S |a_S|^2 + (\Gamma_C + \Gamma_C)|a_S|^2 + \text{Re}(\kappa a_S^* a_C)}.$$

In the limit of weak coupling $|\kappa|^2/\Gamma_S \Gamma_C \ll 1$, the expression reduces to $$\eta' = \frac{|\kappa|^2}{\Gamma_S \Gamma_C} \frac{\Gamma_C \Gamma_L}{(1 + \Gamma_C/\Gamma_L)^2}$$

which is the product of two efficiencies. The left hand factor can be understood as the efficiency of power transfer to the coil in absence of the load. The right-hand factor corresponds to the efficiency of power extraction by the load—this factor is maximized when the impedance-matching condition $\Gamma_C = \Gamma_L$ is satisfied and, as a consequence of the maximum power transfer theorem, is at most 25%. From standard power arguments, it can be shown that the left-hand efficiency is given by $$\frac{|\kappa|^2}{\Gamma_S \Gamma_C} = \frac{\left|\int d^3 r B_S^* \cdot M_C\right|^2}{[\int d^3 r \text{Im} \in (\omega)|E_S|^2][\int d^3 r \text{Im} \in (\omega)|E_C|^2]} \quad (S1)$$

which is the efficiency in Eq. 2. Equivalent expressions can be obtained using other models for coupled electrical systems, such as a two-port lumped element network.

Penetration of time-varying fields in tissue. Although electromagnetic waves varying in time at high frequencies (>100 MHz) are associated with high absorption in tissue, optimal transfer in FIG. 9A is found to occur in the low-gigahertz range. To understand this result, we consider the penetration of a plane wave $H_x(z, t) = H_0 \exp(i(kz - \omega t))$ into a z<0 tissue half-space as the frequency $\omega$ varies. The depth at which the field extends into tissue is described by the skin depth $\delta := 1/\text{Im}(k)$ where $k = \omega\sqrt{\mu \in}$ is the wavenumber. Dispersion in tissue can be described by Debye relaxation $\in/\in_0 = \in_\infty + \Delta E/(1-i\omega\tau_D) + i\sigma/(\omega\in_0)$ where $\Gamma$ is the conductivity, $\tau_D$ the characteristic relaxation time of the medium, $\in_\infty$ the permittivity in the high frequency limit, and $\Delta\in := \in_S - \in_\infty$ ($\in_S$ the static permittivity). The model is valid in the regime $\omega\tau_D \ll 1$, in which case the permittivity can also be approximated as $$\in/\in_0 \approx \in_S[1 + i(\omega\tau_D \Delta\in/\in_S + 1/\omega\tau_E)] \quad (S2)$$

where $\tau_E := \in_0 \in_S/\sigma$ is the electric time constant. The relative significance of $\omega\tau_E$ and $1/\omega\tau_D$ determines the imaginary term's characteristic dependence on $\omega$:

1. At low frequencies when $\omega\tau_E \ll 1$, the permittivity reduces $\epsilon/\epsilon_0 \approx i\epsilon_S/\omega\tau_E$. The wavenumber is given by $k \approx \sqrt{\omega\mu_0/2}(1+i)$, from which one obtains the usual skin depth for conductors $\delta \approx \sqrt{2/\omega\mu_0\sigma}$.

2. When $\omega\tau_E \gg 1$ but $\omega\tau_E \ll 1/\omega\tau_D$, the $\tau_D$ term in Eq. S2 can be neglected such that $$\delta \approx 2\tau_E/\mu_0\epsilon_0\epsilon_S.$$

3. At high frequencies when $\omega\tau_E \gg 1/\omega\tau_D$, we approximate the permittivity as $\epsilon/\epsilon_0 \approx \epsilon_S(1+i\omega\tau_D\Delta\epsilon/\epsilon_S)$. The skin depth is then given by $\delta \approx 2\epsilon_S/(\omega^2\tau_D\Delta\epsilon\sqrt{\mu_0\epsilon_0\epsilon_S})$.

The parameter $1/\tau_E$ and the geometric mean of $1/\tau_E$ and $1/\tau_D$ demarcate three frequency regimes $$\delta \propto \begin{cases} 1/\sqrt{\omega}, & \omega \ll 1/\tau_E \\ O(1), & 1/\tau_E \ll \omega \ll 1/\sqrt{\tau_D\tau_E} \\ 1/\omega^2, & \omega \gg 1/\sqrt{\tau_D\tau_E}. \end{cases}$$

Contrary to the notion that losses consistently increase with frequency, we find that there exists an intermediate range of frequencies across which the penetration is approximately constant. This behavior occurs when the typical time scale of an amplitude variation is much shorter than $\tau_E$ but substantially longer than $\tau_D$. If one operates in this regime, the penetration is expected to be much greater than that naively extrapolated from a low-frequency conductor model of tissue. For the muscle tissue parameters, we calculate the range to be approximately between 690 MHz and 2.2 GHz, which is consistent with our implementation of midfield power transfer.

State-of-the art integrated electronics. To illustrate the range of applications available with performance characteristics reported in the main paper, FIG. 16 describes the power requirements of selected state-of-the-art integrated circuits (ICs). The table is not exhaustive, but is representative of existing solid-state circuit capabilities in the microwatt power regime. With the exception of (31), all devices are currently powered with either wire tethers or large (>2 cm) near-field coils. For stimulation, a local field sensing IC was developed by Medtronic to enable closed-loop neurostimulation (32). As an alternative to electrical stimulation, an optogenetic stimulator consuming 400 µW was designed, with possibility of lower requirements by using more efficient LEDs or opsins (33). Using a more advanced process node and sub-threshold design techniques enabled a reduced power consumption of 0.73 µW, as demonstrated for neural recording (34). Less than 100 µW was required for 100-channel neural recording. A pacemaker IC, developed by St. Jude Medical, contains amplifiers, filters, ADCs, battery management system, voltage multipliers, high voltage pulse generators, programmable logic, and timing control; and consumes only 8 µW (24). A wide dynamic range bio-impedance sensor was also shown to extract QRS features for the detection of ventricular fibrillation (35).

ICs developed for monitoring physiological processes include a fluorimeter for continuous glucose monitoring (36), a cubic-millimeter intraocular pressure sensor (37), and a temperature sensor with an accuracy of ±0.15° C. (38). These sensors require energy in the range of nJ to µJ per measurement. For imaging, a sensor consuming only 3.4 µJ per frame of 256×256 pixels with 8 bits per pixel has been demonstrated (39). An implantable device capable of locomotion in fluid has also been developed (31). Wireless communication allow remote control and non-invasive readout of these devices. In (31), the data receiver consumes 0.5 µJ per bit. For the reverse link (from the device to the external source), the power consumption depends on the range, varying between µJ to nJ per bit.

While the present disclosure (which includes the attachments) is amenable to various modifications and alternative forms, specifics thereof have been shown by way of example in the drawings and will be described in further detail. It should be understood that the intention is not to limit the disclosure to the particular embodiments and/or applications described. Various embodiments described above and shown in the figures and attachments may be implemented together and/or in other manners. One or more of the items depicted in the drawings/figures can also be implemented in a more separated or integrated manner, as is useful in accordance with particular applications.

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

What is claimed is:

1. A wireless power system, comprising:
    an external module having one or more sub-wavelength structures configured to transmit wireless power by manipulating evanescent fields outside of tissue to generate propagating fields inside the patient's tissue and thereby generate a spatially focused field in tissue; and
    an implantable module configured to receive the wireless power from the external module, the implantable module including at least one sensor or stimulator configured to sense a parameter of the tissue or apply stimulation to the tissue.

2. The system of claim 1 wherein the at least one sensor is selected from the group consisting of a thermal sensor, a chemical sensor, a pressure sensor, and oxygen sensor, a PH sensor, a flow sensor, an electrical sensor, a strain sensor, a magnetic sensor, and an imaging sensor.

3. The system of claim 1 wherein the at least one stimulator is selected from the group consisting of an electrical stimulator, an optical stimulator, a chemical stimulator, and a mechanical stimulator.

4. The system of claim 1 wherein the implantable device comprises a modular design that allows interchangeable sensors and/or stimulators.

5. The system of claim 1 wherein the one or more sub-wavelength structures are selected from the group consisting of a patch, a PIFA, a slot in a ground plane, a cross slot in a ground plane, an aperture coupled circular slot in a ground plane, and a half slot in a ground plane.

6. The system of claim 1 wherein the external module further comprises:
one or more excitation ports coupled to the one or more sub-wavelength structures;
at least one voltage source coupled to the one or more excitation ports; and
a controller configured to adjust a phase and/or an amplitude delivered to the one or more sub-wavelength structures to adjust a position of a focal point of the spatially focused field in the tissue.

7. The system of claim 6 wherein the controller is configured to detect a power level of received wireless energy from the implanted module, and is configured to provide feedback to automatically adjust the position of the focal point to optimize wireless power transmission.

8. The system of claim 1 wherein the implantable module is configured to be implanted on, in, or near a heart to apply lead less pacing to the heart.

9. The system of claim 1 wherein the implantable module is configured to be implanted on, in, or near a brain to apply deep brain stimulation to the brain.

10. The system of claim 1 wherein the implantable module is configured to be implanted on, in, or near a spinal cord to apply stimulation to the spinal cord.

11. The system of claim 1 wherein the implantable module is configured to be implanted on, in, or near a muscular tissue of the tongue to apply stimulation to the tongue to treat obstructive sleep apnea.

12. A method of providing therapy to a patient, comprising:
transmitting a mid-field propagating wave to a wireless power receiving module to power the module, the transmitting including manipulating evanescent fields outside of the patient's tissue to generate propagating fields inside the patient's tissue and thereby generate a spatially focused field in the tissue;
sensing a parameter of the patient with the wireless power receiving module; and
providing a therapy to the patient with the wireless power receiving module based on the sensed parameter.

13. The method of claim 12, wherein the transmitting step further comprises transmitting the wave with a sub-wavelength structure that produces a magnetic field perpendicular to the wave and parallel to the patient's tissue interface.

14. The method of claim 12, further comprising adjusting a focal point of the propagating wave to optimize wireless power transmission to the module.

15. A method of cardiac pacing in a patient, comprising:
transmitting a mid-field propagating wave to a wireless power receiving module to power the module, the transmitting including manipulating evanescent fields outside of the patient's tissue to generate propagating fields inside the patient's tissue and thereby generate a spatially focused field in the tissue;
sensing a parameter of the patient's heart with the wireless power receiving module; and
providing electrical pacing to the heart with the wireless power receiving module based on the sensed parameter.

16. The method of claim 15, wherein the transmitting step further comprises transmitting the wave with a sub-wavelength structure that produces a magnetic field perpendicular to the wave and parallel to the patient's tissue interface.

17. A method of deep brain stimulation, comprising:
transmitting a mid-field propagating wave to a wireless power receiving module to power the module, the transmitting including manipulating evanescent fields outside of the patient's tissue to generate propagating fields inside the patient's tissue and thereby generate a spatially focused field in the tissue;
sensing a parameter of the brain with the wireless power receiving module; and
providing stimulation to the brain with the wireless power receiving module based on the sensed parameter.

18. The method of claim 17, wherein the transmitting step further comprises transmitting the wave with a sub-wavelength structure that produces a magnetic field perpendicular to the wave and parallel to the patient's tissue interface.

19. A method of stimulating tissue, comprising:
transmitting a mid-field propagating wave to a wireless power receiving module to power the module, the transmitting including manipulating evanescent fields outside of the patient's tissue to generate propagating fields inside the patient's tissue and thereby generate a spatially focused field in the tissue;
sensing a parameter of the tissue with the wireless power receiving module; and
providing stimulation to the tissue with the wireless power receiving module based on the sensed parameter.

20. The method of claim 19 further comprising adjusting a focal point of the propagating wave to optimize wireless power transmission to the module.

21. The method of claim 19 wherein the transmitting step comprises transmitting the wave with a sub-wavelength structure that produces a magnetic field perpendicular to the wave and parallel to a tissue interface.

22. An apparatus configured to transfer wireless power through tissue, comprising:
a substrate;
at least one sub-wavelength structure disposed on the substrate;
at least one radio-frequency port coupled to the at least one sub-wavelength structure;
a voltage or current source coupled to the at least one radio-frequency port; and
a controller configured to manage excitation of the at least one radio-frequency port and sub-wavelength structure with the voltage or current source to manipulate evanescent fields outside of tissue to generate propagating fields inside the tissue and thereby generate a spatially focused field in the tissue.

23. The apparatus of claim 22, wherein each of the at least one sub-wavelength structure is coupled to a respective independent radio-frequency port.

24. An apparatus configured to transfer wireless power through tissue, comprising:
a plurality of sub-wavelength structures configured and arranged to generate propagating fields inside tissue and thereby generate a spatially adaptable electromagnetic field in the tissue;
a plurality of independent feed ports configured and arranged to individually excite a respective one of the plurality of sub-wavelength structures thereby generating the spatially adaptable electromagnetic field; and
a controller configured to control the excitation of the respective sub-wavelength structures to redistribute a peak surface tissue absorption of the electromagnetic field.

25. The apparatus of claim 24, wherein the plurality of sub-wavelength structures are further configured and arranged to generate an adaptive steering field in tissue.

26. The apparatus of claim 24, wherein the spatially focusing and adaptive steering field/signal has a frequency between 300 MHz and 3000 MHz.

* * * * *